United States Patent [19]

Shiono et al.

[11] Patent Number: 4,523,024
[45] Date of Patent: Jun. 11, 1985

[54] 3,4-DIHYDRO-2H-BENZOPYRAN DERIVATIVES, A METHOD OF PRODUCING THEM, A METHOD OF USING THEM AS STABILIZERS FOR ORGANIC MATERIALS, AND ORGANIC COMPOSITIONS CONTAINING SUCH STABILIZERS

[75] Inventors: Manzo Shiono; Yoshiji Fujita; Takashi Nishida, all of Kurashiki, Japan

[73] Assignee: Kuraray Co., Ltd., Kurashiki, Japan

[21] Appl. No.: 552,068

[22] Filed: Nov. 15, 1983

[30] Foreign Application Priority Data

Nov. 26, 1982 [JP] Japan ................................ 57-208252
Dec. 27, 1982 [JP] Japan ................................ 57-229693
Mar. 3, 1983 [JP] Japan ................................ 58-35599
Apr. 1, 1983 [JP] Japan ................................ 58-58179
Oct. 14, 1983 [JP] Japan ................................ 58-193179

[51] Int. Cl.$^3$ ............................................ C07D 311/72
[52] U.S. Cl. ................................ 549/407; 549/389; 549/214; 549/411; 524/110; 585/3; 523/202
[58] Field of Search ...................... 549/407, 389, 214

[56] References Cited

U.S. PATENT DOCUMENTS 4,127,608 11/1978 Olson et al. .......................... 549/407
4,374,258 2/1983 Horner et al. ....................... 549/407

Primary Examiner—Nicky Chan
Attorney, Agent, or Firm—Oblon, Fisher, Spivak, McClelland & Maier

[57] ABSTRACT

There is provided a class of novel 3,4-dihydro-2H-benzopyran derivatives which either have excellent inhibitory activity against unfavorable effects of heat, light and oxidative factors or are of use as precursors of compounds having such activity, and methods for producing these derivatives. Also provided are methods of using such 3,4-dihydro-2H-benzopyran derivatives as stabilizers for organic materials sensitive to heat, light or/and oxidative factors, and organic compositions containing such stabilizers.

22 Claims, No Drawings

3,4-DIHYDRO-2H-BENZOPYRAN DERIVATIVES, A METHOD OF PRODUCING THEM, A METHOD OF USING THEM AS STABILIZERS FOR ORGANIC MATERIALS, AND ORGANIC COMPOSITIONS CONTAINING SUCH STABILIZERS

BACKGROUND OF THE INVENTION

1. Field of the Invention

The present invention relates to a 3,4-dihydro-2H-benzopyran derivative of general formula (I)

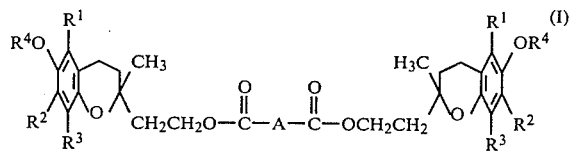

wherein $R^1$ is a hydrogen atom or a lower alkyl group; $R^2$ and $R^3$ are the same or different and each is a hydrogen atom, a lower alkyl group or a lower alkoxy group, or $R^2$ and $R^3$ taken together represent a group of the formula $-CH=CH-CH=CH-$; $R^4$ is a hydrogen atom or a hydroxy-protecting group; A is a group selected from the class consisting of $-(CH_2)_n-$, phenylene, $-CH_2SCH_2-$, $-CH_2CH_2SCH_2-$, $-CH_2CH_2SCH_2CH_2-$, $-CH_2S-SCH_2-$, $-CH_2CH_2S-SCH_2CH_2-$, $-CH_2SCH_2SCH_2-$, $-CH_2CH_2SCH_2SCH_2CH_2-$,

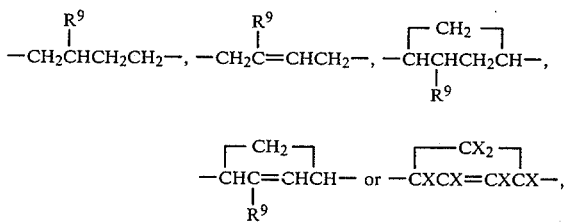

where n is an integer equal to or greater than 1; $R^5$ and $R^6$ are the same or different and each is a hydrogen atom or a lower alkyl group or taken together represent a group of $-(CH_2)_4-$; $R^7$ and $R^8$ taken together represent $$-CH_2CHCH_2CH_2-, \quad -CH_2C=CHCH_2-, \quad -CHCHCH_2CH-,$$
$$\overset{|}{R^9} \quad \overset{|}{R^9} \quad \overset{|}{R^9}$$

$$-CHC=CHCH- \text{ or } -CXCX=CXCX-,$$

$R^9$ is a hydrogen atom or a lower alkyl group and X is a halogen atom, and a method of producing said 3,4-dihydro-2H-benzopyran derivative.

In further aspects, the present invention relates to a method of using a compound of the above general formula wherein $R^4$ is a hydrogen atom, i.e. a 3,4-dihydro-6-hydroxy-2H-benzopyran derivative of the following general formula (I') as a stabilizer for organic materials and an organic composition containing the same stabilizer.

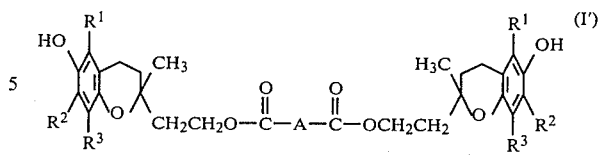

2. Description of the Prior Art

The 3,4-dihydro-2H-benzopyran derivatives of general formula (I) as provided by the present invention are novel compounds which have not been described in the prior art literature. Among these 3,4-dihydro-2H-benzopyran derivatives, the compounds of general formula (I) wherein $R^4$ is a hydrogen atom, that is the 3,4-dihydro-6-hydroxy-2H-benzopyran derivatives of general formula (I'), have excellent antagonistic and preventive actions against unfavorable effects due to heat, light and oxidative factors and are of use as stabilizers for organic materials sensitive to heat, light or/and oxidizing factors, such as oils and fats, waxes, pharmaceutical compositions and preparations, cosmetic products, rubber products, synthetic resins, etc. Moreover, the compounds of general formula (I) wherein $R^4$ is a hydroxy-protecting group can be easily converted to those 3,4-dihydro-6-hydroxy-2H-benzopyran derivatives (I') possessing the aforementioned antagonistic and preventive actions by substituting a hydrogen atom for said protecting group in accordance with the per se conventional procedure.

Recently attention has been focused on vitamin E as a safe antioxidant but as it is comparatively expensive and ready to be oxidized and discolor, it has not been commonly employed for antioxidative purposes.

SUMMARY OF THE INVENTION

The present invention has one of its objects to provide novel 3,4-dihydro-2H-benzopyran derivatives having the general formula (I) which either have an excellent preventive effect against unfavorable effects due to heat, light and oxidative factors or are precursors of compounds having such preventive effect.

It is another object of the present invention to provide novel 3,4-dihydro-2H-benzopyran derivatives which either have an antioxidant property superior to that of vitamin E or are precursors of compounds having such property.

It is another object of the present invention to provide a method of producing the aforementioned novel and useful 3,4-dihydro-2H-benzopyran derivatives.

It is still another object of the present invention to provide a method of using a 3,4-dihydro-6-hydroxy-2H-benzopyran derivative of general formula (I') as a stabilizer for organic materials.

It is a further object of the present invention to provide an organic composition containing a 3,4-dihydro-6-hydroxy-2H-benzopyran derivative of general formula (I') as a stabilizer.

These objects as well as other objects and advantages of the present invention will become apparent to those skilled in the art from the following detailed description.

DETAILED DESCRIPTION OF THE INVENTION

Referring, first, to the above general formula (I), $R^1$ represents a hydrogen atom or a lower alkyl group such as methyl, ethyl, propyl, butyl, etc. $R^2$ and $R^3$ are the same or different and each represents a hydrogen atom, a lower alkyl group such as methyl, ethyl, propyl, butyl, etc. or a lower alkoxy group such as methoxy, ethoxy, propoxy, butoxy, etc., or $R^2$ and $R^3$ taken together represent a group of —CH=CH—CH=CH—. $R^4$ is a hydrogen atom or a hydroxy-protecting group. The hydroxy-protecting group may be any of the protecting groups which are commonly employed for protection of hydroxy groups, and may be exemplified by acyl groups such as acetyl, propionyl, butyryl, benzoyl, etc., methyl, t-butyl, triphenylmethyl, benzyl, trimethylsilyl and so on. A represents a group selected from the class consisting of $(CH_2$—$)_n$, phenylene, —$CH_2SCH_2$—, —$CH_2CH_2SCH_2$—, —$CH_2CH_2SCH_2CH_2$—, —$CH_2S$—$SCH_2$—, —$CH_2CH_2S$—$SCH_2CH_2$—, —$CH_2SCH_2SCH_2$—, —$CH_2CH_2SCH_2SCH_2CH_2$—,

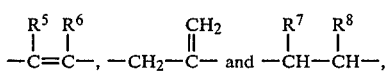

wherein n is an integer equal to or greater than 1 but in view of the availability of the material dicarboxylic acid, the value of n is preferably in the range of 1 to 14 and more desirably in the range of 1 to 8. $R^5$ and $R^6$ are the same or different and each is a hydrogen atom or a lower alkyl group such as methyl, ethyl, propyl, butyl, etc., or $R^5$ and $R^6$ taken together represent a group of —$(CH_2)_4$—. $R^7$ and $R^8$ taken together represent

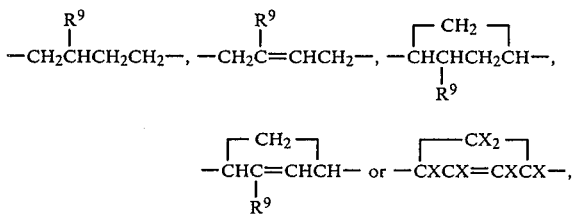

wherein $R^9$ is a hydrogen atom or a lower alkyl group such as methyl, ethyl, propyl, butyl, etc. and X is a halogen atom such as chlorine, bromine, iodine, etc.

In accordance with the present invention, a 3,4-dihydro-2H-benzopyran derivative of general formula (I) can be produced by reacting a 2-substituted ethyl alcohol of general formula (II)

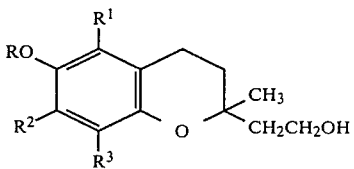

wherein $R^1$, $R^2$ and $R^3$ are respectively as defined in general formula (I); R is a hydrogen atom or a hydroxy-protecting group and may be the same as or different from $R^4$ in general formula (I), or a reactive derivative thereof with a dicarboxylic acid of general formula (III)

wherein A is as defined in general formula (I), or a reactive derivative thereof. The reactive derivative of 2-substituted ethyl alcohol is exemplified by the corresponding halides, alkanesulfonates, arenesulfonates, carboxylates, etc. The reactive derivative of dicarboxylic acid is exemplified by the corresponding lower alkyl esters, acid halides, acid anhydrides or mixed acid anhydrides, alkali metal salts, silver salt, and salts with organic tertiary or quaternary bases.

The reaction between said 2-substituted ethyl alcohol (II) or reactive derivative thereof and said dicarboxylic acid (III) or reactive derivative thereof can be conducted under the conventional conditions of ester synthesis. The following are a few typical examples of such ester synthesis reactions.

REACTION EXAMPLE (a)

Reaction between alcohol and dicarboxylic acid dihalide

The alcohol (II) and a dihalide of dicarboxylic acid (III), preferably the dichloride of dicarboxylic acid (III), are reacted in an inert solvent such as benzene, toluene, ether, chloroform, etc. and in the presence of 1 to 3 molar equivalents, based on the alcohol, of a tertiary amine such as pyridine, triethylamine, etc. at room temperature to give the desired 3,4-dihydro-2H-benzopyran derivative (I).

REACTION EXAMPLE (b)

Reaction between alcohol and acid anhydride or mixed acid anhydride

The alcohol (II) and the acid anhydride of dicarboxylic acid (III) or a mixed acid anhydride of dicarboxylic acid (III) with, for example, pivalic acid, p-toluenesulfonic acid, etc. are reacted in an inert solvent such as benzene, toluene, xylene, hexane, etc. and preferably in the presence of an acid, e.g. sulfuric acid, p-toluenesulfonic acid, etc. or a tertiary amine, e.g. pyridine, triethylamine, etc. at room temperature or under mild heating and, if necessary, the reaction product is further caused to undergo dehydrative condensation to give the desired 3,4-dihydro-2H-benzopyran derivative (I).

REACTION EXAMPLE (c)

Reaction between alcohol and dicarboxylic acid

The alcohol (II) and the dicarboxylic acid (III) are reacted in an inert solvent such as benzene, toluene, xylene, etc. and in the presence of a dehydrative condensing agent such as dicyclohexylcarbodiimide, a combination of 2-chloro-1-methylpyridinium iodide and triethylamine, etc. at room temperature or under mild heating, or reacted under azeotropic dehydration conditions to give the desired 3,4-dihydro-2H-benzopyran derivative (I).

REACTION EXAMPLE (d)

Reaction between alcohol and dicarboxylic acid lower alkyl ester

The alcohol (II) and a lower alkyl ester of the dicarboxylic acid (III) are reacted under heating in an inert solvent such as toluene, xylene, etc. and in the presence of a suitable transesterification catalyst e.g. p-toluenesulfonic acid or a titanium compound such as tetramethyl titanate, with the byproduct low-boiling alcohol being removed from the reaction system, to give the desired 3,4-dihydro-2H-benzopyran derivative (I).

REACTION EXAMPLE (e)

Reaction between a halide, alkanesulfonate or arenesulfonate of alcohol and an alkali metal salt, silver salt or organic tertiary or quaternary base salt of dicarboxylic acid A halide, alkanesulfonate or arenesulfonate of the alcohol (II) and an alkali metal salt, silver salt or organic tertiary or quaternary base salt of the dicarboxylic acid (III) are reacted in a solvent such as dimethylformamide, benzene, acetone, etc. at room temperature or under mild heating to give the desired 3,4-dihydro-2H-benzopyran derivative (I).

Separation and recovery of the 3,4-dihydro-2H-benzopyran derivative produced by any of the above ester synthesis reactions can be accomplished in the per se known manner. For example, the reaction mixture is first diluted with water and then extracted with an extractant such as ether, etc. The extract is washed with water and dried and the solvent is then distilled off. The residue is purified by recrystallization or column chromatography. In the above manner, the 3,4-dihydro-2H-benzopyran derivative of general formula (I) can be isolated and purified.

Referring to the 2-substituted ethyl alcohol of general formula (II) as a starting compound, a large majority of its species are known compounds (see German Offenlegungsschrift No. 2364141 and German Offenlegungsschrift No. 3010504) and according to the method previously found by the present inventors, it can be easily provided by reacting a hydroquinone compound of the general formula (IV)

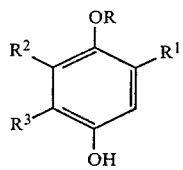

wherein R, $R^1$, $R^2$ and $R^3$ are as defined in general formula (II) with 4-methyl-5,6-dihydro-2H-pyran in the presence of a Lewis acid (see Japanese Patent Application No. 57-83654). As examples of the Lewis acid useful for this condensation reaction, there may be mentioned boron trifluoride-ether complex, aluminum chloride, aluminum bromide, ferrous chloride, ferric chloride, stannous chloride, stannic chloride, zinc chloride, sulfuric acid, p-toluenesulfonic acid, etc., although aluminum chloride and boron trifluoride-ether complex are particularly desirable. The proportion of the Lewis acid relative to the hydroquinone compound of general formula (IV) is about 0.1 to 2 molar equivalents and preferably about 0.5 to 1.0 molar equivalents. This condensation reaction is preferably conducted in a solvent. The solvent is exemplified by halogenated hydrocarbons such as 1,2-dichloroethane, dichloromethane, chloroform, 1,1,2-trichloroethylene, carbon tetrachloride, chlorobenzene, etc.; hydrocarbons such as benzene, toluene, xylene, cyclohexane, n-hexane, ligroin, etc.; nitrogen-containing compounds such as nitromethane, nitrobenzene, benzonitrile, acetonitrile, etc.; oxygen-containing compounds such as methyl ethyl ketone, ethyl acetate, butyl acetate, etc.; and mixtures of such solvents. Particularly preferred is 1,2-dichloroethane. The proportion of the solvent relative to each one weight part of the hydroquinone compound of general formula (IV) is about 2 to 100 weight parts and preferably about 5 to 20 weight parts. This condensation reaction is conducted generally at −40° C. to +150° C. and preferably at 0° C. to 100° C.

The 2-substituted ethyl alcohol of general formula (II) can be halogenated, alkanesulfonylated, arenesulfonylated or acylated in the conventional manner to the aforesaid reactive derivative of 2-substituted ethyl alcohol.

The dicarboxylic acid of general formula (III), a mating compound, is a known compound, and includes such species as malonic acid, succinic acid, glutaric acid, adipic acid, pimelic acid, suberic acid, azelaic acid, sebacic acid, brassylic acid, thapsic acid, phthalic acid, isophthalic acid, terephthalic acid, thiodiglycolic acid, thiodipropionic acid, 3-thia-1,6-hexanedioic acid, 3,4-dithia-1,6-hexanedioic acid, 4,5-dithia-1,8-octanedioic acid, 3,5-dithia-1,7-heptanedioic acid, 4,6-dithia-1,9-nonanedioic acid, maleic acid, fumaric acid, itaconic acid, citraconic acid, 4-cyclohexene-1,2-dicarboxylic acid, 4-methyl-4-cyclohexene-1,2-dicarboxylic acid, 1-cyclohexene-1,2-dicarboxylic acid, cyclohexane-1,2-dicarboxylic acid, 5-norbornene-2,3-dicarboxylic acid, 5-methyl-5-norbornene-2,3-dicarboxylic acid, 1,4,5,6,7,7-hexachloro-5-norbornene-2,3-dicarboxylic acid, norbornane-2,3-dicarboxylic acid, etc. These dicarboxylic acids can be easily converted by the conventional procedures to such reactive derivatives as the corresponding lower alkyl esters, acid halides, acid anhydrides, mixed acid anhydrides, alkali metal salts, silver salts, or salts with organic tertiary or quaternary bases.

In accordance with the present invention, the 3,4-dihydro-2H-benzopyran derivative of general formula (I) can also be produced by reacting a hydroquinone compound of general formula (IV) with a dicarboxylic acid ester of general formula (V)

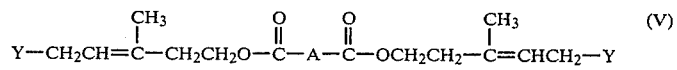

wherein Y is a halogen atom and A is as defined in general formula (I), in the presence of a Lewis acid.

The Lewis acid as used in this condensation reaction is exemplified by boron trifluoride-ether complex, aluminum chloride, aluminum bromide, ferrous chloride, ferric chloride, stannous chloride, stannic chloride, zinc chloride, etc. Preferred is zinc chloride. The proportion of the Lewis acid relative to the hydroquinone compound of general formula (IV) is about 0.0001 to 1 molar equivalent and preferably about 0.001 to 0.1 molar equivalent. This condensation reaction is preferably conducted in a solvent, and those solvents mentioned for use in the aforementioned condensation reaction between the hydroquinone compound of general formula (IV) and 4-methyl-5,6-dihydro-2H-pyran can be employed for this reaction. The proportion of the solvent relative to the hydroquinone compound (IV) is about 2 to 100 times by weight and preferably about 5 to 20 times by weight. This condensation reaction is carried out generally at about −40° C. to +150° C. and preferably at 0° C. to 100° C.

The dicarboxylic acid ester of general formula (V) used as a starting compound can be easily prepared by reacting 4-methyl-5,6-dihydro-2H-pyran with a halide of the dicarboxylic acid of general formula (III) in the presence of a Lewis acid. This condensation reaction can be conducted in the presence of a Lewis acid such as those mentioned for use in the condensation reaction between said hydroquinone compound (IV) and said dicarboxylic acid ester (V). The proportion of the Lewis acid relative to 4-methyl-5,6-dihydro-2H-pyran is 0.001 to 0.5 molar equivalent and preferably 0.01 to 0.5 molar equivalent. This condensation reaction is preferably conducted in a solvent and the solvents mentioned for use in the aforementioned condensation reaction between said hydroquinone compound (IV) and said dicarboxylic acid ester (V) can be employed for this reaction. The proportion of the solvent relative to 4-methyl-5,6-dihydro-2H-pyran is about 2 to 100 times by weight and preferably about 5 to 20 times by weight. This condensation reaction is conducted generally at −5° C. to +70° C. and preferably at 0° to 50° C. The resulting reaction mixture containing the dicarboxylic acid ester of general formula (V) can be directly subjected to the reaction with a hydroquinone compound of general formula (IV).

The following is a preferred procedure for the production of a 3,4-dihydro-2H-benzopyran derivative of general formula (I) by the steps comprising reacting 4-methyl-5,6-dihydro-2H-pyran with a halide of the dicarboxylic acid of general formula (III) to give a dicarboxylic acid ester of general formula (V) and reacting this ester (V) with a hydroquinone compound of general formula (IV). First, 4-methyl-5,6-dihydro-2H-pyran and a Lewis acid are dissolved or suspended in a solvent and, then, a halide of the dicarboxylic acid of general formula (III) is added. The mixture is stirred for about 0.5 to 4 hours to give a reaction mixture containing the corresponding dicarboxylic acid ester of general formula (V). From this reaction mixture, the dicarboxylic acid ester of general formula (V) is separated, for example by distillation. Then, the hydroquinone compound of general formula (IV) and the Lewis acid are dissolved or suspended in a solvent, and in an inert gas such as nitrogen gas, etc. and under constant stirring and heating, 0.5 to 0.6 molar equivalent of the dicarboxylic acid ester of general formula (V) relative to the hydroquinone compound (IV) is added over a period of about 0.5 to 8 hours. After addition of the dicarboxylic acid ester of general formula (V), the mixture was further stirred for about 0.5 to 4 hours, whereby a reaction mixture containing the 3,4-dihydro-2H-benzopyran derivative of general formula (I) is obtained. The separation and recovery of the 3,4-dihydro-2H-benzopyran derivative from the above reaction mixture can be easily accomplished by the procedure set forth hereinbefore.

The 2-substituted ethyl alcohol of general formula (II) or reactive derivative thereof and the dicarboxylic acid ester of general formula (V), which are used as starting materials in the process for production of the 3,4-dihydro-2H-benzopyran derivative of general formula (I) according to the present invention, can be easily derived from 4-methyl-5,6-dihydro-2H-pyran as mentioned hereinbefore, while said 4-methyl-5,6-dihydro-2H-pyran is available in large quantities as a by-product in the production of isoprene from isobutene and formalin and can also be synthesized easily and at low cost by the reaction of tert-butanol and aqueous formaldehyde in the presence of an acid catalyst, for instance.

In a further aspect of the present invention, among the 3,4-dihydro-2H-benzopyran derivatives of general formula (I), the thiodipropionate of general formula (I″)

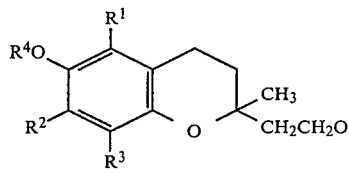 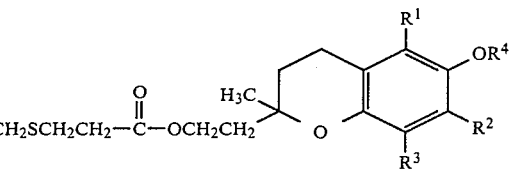

wherein $R^1$, $R^2$, $R^3$ and $R^4$ are as defined in the general formula (I), can also be produced by reacting a 2-substituted ethyl acrylate of the general formula (VI)

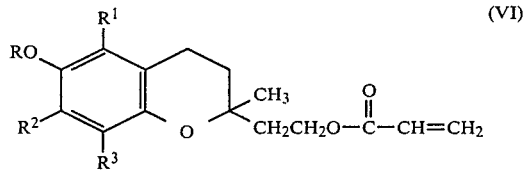 (VI)

wherein R, $R^1$, $R^2$ and $R^3$ are as defined in the general formula (II), with hydrogen sulfide in the presence of a basic catalyst.

The basic catalyst used in this reaction is exemplified by sodium acetate; alkali metal hydroxides such as sodium hydroxide, potassium hydroxide, etc.; alkali metal alcoholates such as sodium methylate, sodium ethylate, potassium methylate, potassium ethylate, potassium t-butylate, etc.; tertiary amines such as pyridine, triethylamine, etc.; basic ion exchange materials and so on. The basic catalyst is preferably used in a proportion of 0.1 to 10 weight percent relative to the 2-substituted ethyl acrylate of general formula (VI). This reaction is preferably conducted in a solvent. As examples of the solvent may be mentioned 1,2-dichloroethane, methylene chloride, tetrahydrofuran, diethyl ether, toluene, xylene, ethanol, isopropyl alcohol, etc. The proportion of the solvent is about 2 to 100 times by weight, preferably about 5 to 20 times by weight based on the 2-substituted ethyl acrylate of general formula (VI). While this reaction may be conducted at room temperature, it is preferably carried out under warming or heating.

The majority of the 2-substituted ethyl acrylates of general formula (VI) are known compounds, and these compounds can be easily produced by subjecting a 2-substituted ethyl alcohol of general formula (II) and methyl acrylate to a transesterification reaction.

Separation and recovery of the thiodipropionic acid ester of general formula (I″) produced by the reaction of a 2-substituted ethyl acrylate of general formula (VI) with hydrogen sulfide can be easily accomplished by the procedure described hereinbefore.

The 3,4-dihydro-6-hydroxy-2H-benzopyran derivative of general formula (I′) according to the present invention is used as a stabilizer for organic materials sensitive to heat, light or oxidative factors, such as oils and fats, waxes, pharmaceutical products, cosmetic products, rubber products, synthetic resins, etc., by adding the same derivative to said organic materials. This stabilizer can be desirably used in conjunction with such organic materials as the oils and fats and foodstuffs containing unsaturated fatty acids (e.g. oleic acid, linoleic acid, linolenic acid, arachidonic acid, etc.) or esters thereof; and synthetic resins including polyolefins such as polyethylene, polypropylene, ethylene-propylene copolymer, etc.; diene polymers such as polybutadiene, polyisoprene, ethylene-propylenediene terpolymer, etc.; styrenic resins such as polystyrene, styrene-butadiene copolymer, styrene-acrylonitrile copolymer, methacrylate-styrene-acrylonitrile copolymer, ABS resin, etc.; halogen-containing resins such as polyvinyl chloride, polyvinylidene chloride, vinyl chloride-vinylidene chloride copolymer, polychloroprene, chlorinated polyethylene, etc.; polymers of $\alpha,\beta$-unsaturated acids or derivatives thereof such as polyacrylates, polyacrylamide, polyacrylonitrile, etc.; polymers of unsaturated alcohols or acyl derivatives thereof such as polyvinyl alcohol, polyvinyl acetate, styrene-vinyl acetate copolymer, etc.; polyurethane; aliphatic or aromatic polyamides; polyimides, poly(amide-imide); polyacetal; polycarbonate; saturated or unsaturated polyesters; epoxy resins; phenolic resins; polyphenylene oxide; urea resin; melamine resin; etc. While the amount of the stabilizer should vary with the required degree of stabilization effect sought in the organic material, it can be selected from the range of about 0.001 to 20 weight percent relative to the organic material. For the stabilization of a synthetic resin, the stabilizer can be used advantageously in an amount from about 0.001 to 5 weight percent based on the resin and when the organic material is a highly sensitive material such as a vitamin, the amount of the stabilizer may be increased to about 20 weight percent.

The 3,4-dihydro-6-hydroxy-2H-benzopyran derivative of general formula (I′) according to the present invention is used either alone or in combination with one or more other stabilizers, particularly phenolic stabilizers such as pentaerythritol tetrakis[3-(3,5-di-tert-butyl-4-hydroxyphenyl)propionate], octadecyl 3-(3,5-di-tert-butyl-4-hydroxyphenyl)propionate, etc. These phenolic and other stabilizers are generally used in a proportion of about 10 to 500 weight percent relative to the compound of the present invention. Further, the compound according to the present invention can be used in combination with synergistic auxiliary stabilizers such as calcium stearate, distearyl thiodipropionate, etc. These auxiliary stabilizers are used in a proportion of about 50 to 500 weight percent relative to the compound of the present invention.

Thus, the organic composition prepared by incorporating a 3,4-dihydro-6-hydroxy-2H-benzopyran derivative of general formula (I′) according to the present invention in an organic material is very stable against adverse effects due to heat, light and oxidative factors. The term "unfavorable effects" as used herein means the degradation, decomposition, etc. of organic materials. Taking synthetic resins as an example, the adverse effects include the decomposition and undesirable crosslinking of macromolecules, and other changes which manifest as aging, brittleness, discoloration, depression of softening point, etc.

Synthesis Examples of the compounds according to the present invention, and test examples and working effect examples using these compounds are given below. It should be understood that the present invention is not limited to these specific examples.

SYNTHESIS EXAMPLE 1

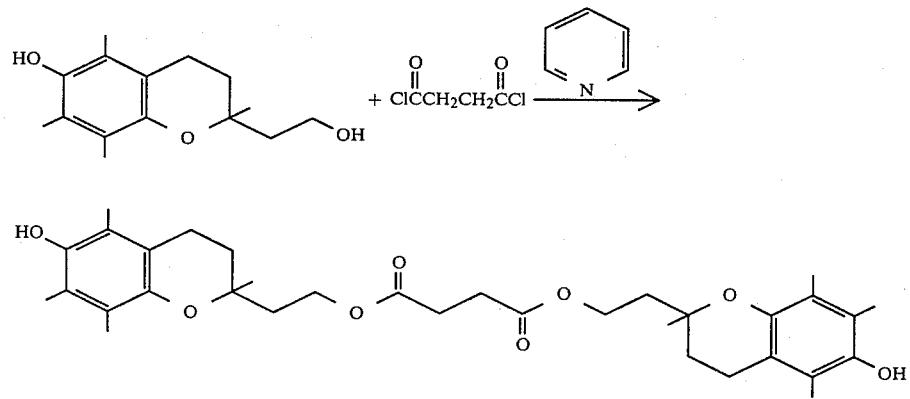

Succinyl chloride (5 mmol) was added dropwise to a mixture of 2.5 g of 3,4-dihydro-2-(2-hydroxyethyl)-2,5,7,8-tetramethyl-2H-benzopyran-6-ol, 0.79 g of pyridine and 10 ml of methylene chloride with ice-cooling. The mixture was stirred at room temperature overnight. Then, water was added, and the mixture was extracted with diethyl ether. The extract was washed with water, dried over anhydrous magnesium sulfate and concentrated. The concentrate was purified by silica gel column chromatography to give 2.54 g (87.3%) of di-[2-(3,4-dihydro-6-hydroxy-2,5,7,8-tetramethyl-2H-benzopyranyl)ethyl] succinate, which showed the following NMR spectrum.

NMR spectrum (90 MHz) $\delta_{CDCl_3}^{HMS}$: 1.23 (s, 6H); 1.53–2.2 (m, 26H); 2.4–2.75 (m, 8H); 4.05–4.43 (m, 4H), 4.72 (br. s, 2H).

SYNTHESIS EXAMPLES 2 TO 9

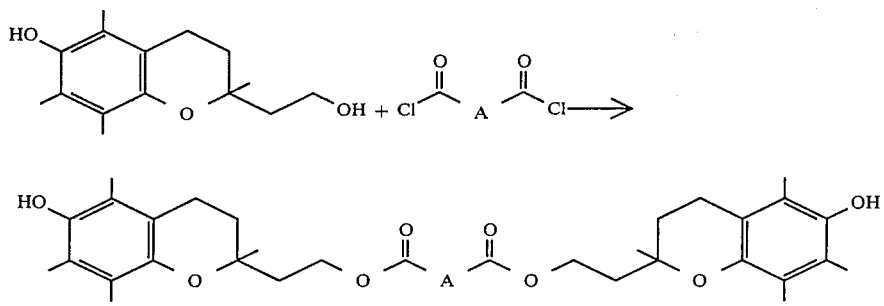

The same reaction and isolation procedures as Synthesis Example 1 were followed except that 5 millimoles each of the dicarboxylic acid chlorides of Table 1 was used in lieu of 5 millimoles of succinyl chloride to give the corresponding 3,4-dihydro-2H-benzopyran derivative. The yield, NMR spectrum and FD mass spectrum of each product are given in Table 1.

SYNTHESIS EXAMPLE 10

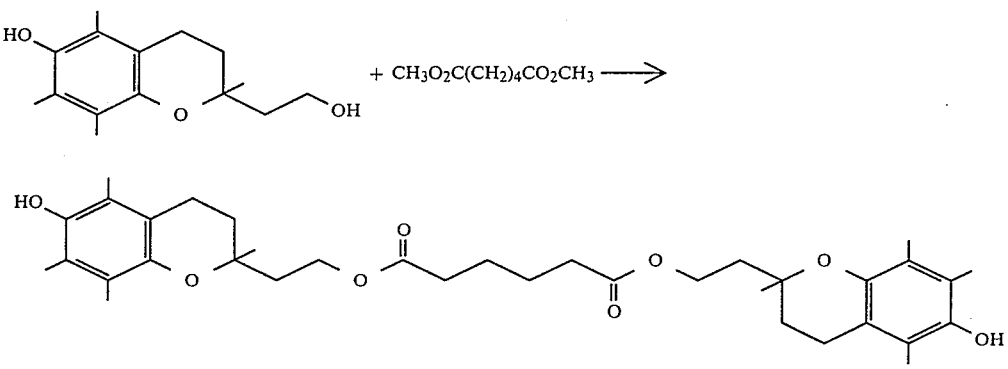

A mixture of 1.74 g of methyl adipate, 4.76 g of 3,4-dihydro-2-(2-hydroxyethyl)-2,5,7,8-tetramethyl-2H-benzopyran-6-ol, 0.24 g of tetraisopropoxytitanium and 100 ml of toluene was heated and, while the byproduct methanol and the toluene being gradually distilled off, 50 ml of toluene was added gradually. The mixture was

TABLE 1

| Synthesis Example | Dicarboxylic acid chloride | A | Yield (%) | NMR spectrum (90MHz) $\delta_{CDCl_3}^{HMS}$: | FD mass spectrum |
|---|---|---|---|---|---|
| 2 | Glutaroyl chloride ClCO(CH₂)₃COCl | $-(CH_2)_3-$ | 87.2 | 1.22(s,6H),1.55~2.7(m,36H), 4.05~4.4(m,4H),4.63(s,2H) | [M]⁺ 596 |
| 3 | Adipoyl chloride ClCCO(CH₂)₄COCl | $-(CH_2)_4-$ | 92.7 | 1.23(s,6H),1.47~2.35(m,34H), 2.57(t, J = 7Hz, 4H), 4.05~4.4(m, 6H) | [M + 1]⁺ 611 |
| 4 | Aselaoyl chloride ClCO(CH₂₃)₇COCl | $-(CH_2)_7-$ | 89.6 | 1.24(s, 6H), 1.4~2.35(m, 40H), 2.57(t, J = 7Hz, 4H), 4.06~4.4(m, 6H) | [M]⁺ 652 |
| 5 | Sebacoyl chloride ClCO(CH₂)₈COCl | $-(CH_2)_8-$ | 83.1 | 1.24(s, 6H), 1.3~2.37(m, 42H), 2.57(t, J = 7Hz, 4H), 4.06~4.4(m, 4H), 4.53(s, 2H) | [M]⁺ 666 |
| 6 | Phthaloyl chloride (o-C₆H₄(COCl)₂) | (o-phenylene) | 74.0 | 1.24(s, 6H),1.6~2.2(m, 26H), 2.56(t, J = 7Hz, 4H), 4.22~4.65 (m, 6H), 7.4~7.75(m, 4H) | [M]⁺ 630 |
| 7 | Terephthaloyl chloride (p-C₆H₄(COCl)₂) | (p-phenylene) | 64.0 | 1.3(s, 6H), 1.7~2.2(m, 26H), 2.6(t, J = 7Hz, 4H), 3.74~4.7(m, 6H), 8.05(s, 4H) | [M]⁺ 630 |
| 8 | 1,1 0—Decanedicarbonyl chloride BrCO(CH₂)₁₀COBr | $-(CH_2)_{10}-$ | 72.6 | 1.24(s, 6H), 1.3~2.35(m, 46H), 2.57(t, J = 7Hz, 4H), 4.05~4.4(m, 6H) | [M]⁺ 694 |
| 9 | Hexadecanedioyl chloride ClCO(CH₂)₁₄COCl | $-(CH_2)_{10}-$ | 70.5 | 1.24(s, 6H), 1.3~2.37(m, 54H), 4.05~4.4(m, 6H) | [M]⁺ 750 | stirred at 170° C. for an hour and cooled. Toluene and diethyl ether were added and the mixture was washed with 6N hydrochloric acid and aqueous sodium chloride in that order. The resulting organic layer was dried, concentrated and purified by silica gel column chromatography to give 2.94 g (50.7%) of di[2-(3,4-dihydro-6-hydroxy-2,5,7,8-tetramethyl-2H-benzopyranyl)ethyl] adipate.

SYNTHESIS EXAMPLE 11 pyran-6-ol, 100 ml of toluene and 0.2 g of p-toluenesulfonic acid was heated, with the byproduct water being azeotropically removed. After the reaction was completed, the toluene was distilled off. The cooled residue was extracted with diethyl ether and the extract was washed with water, dried and concentrated. The concentrate was purified by silica gel column chromatography to give 4.27 g (70%) of di[2-(3,4-dihydro-6-hydroxy-2,5,7,8-tetramethyl-2H-benzopyranyl)ethyl] adipate.

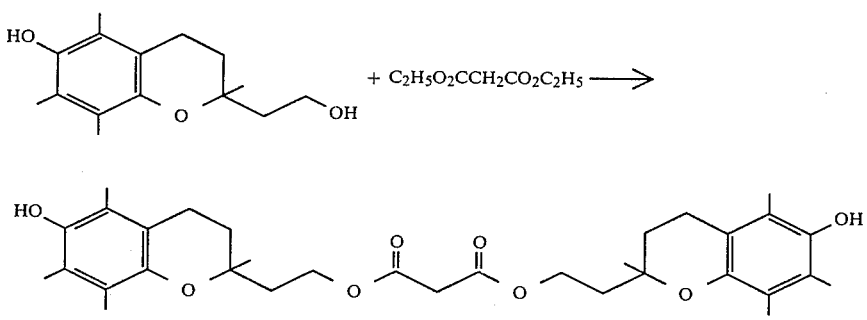

The same reaction and isolation procedures as Synthesis Example 10 were followed except that 1.60 g of ethyl malonate and 0.3 g of p-toluenesulfonic acid were used in lieu of 1.74 g of methyl adipate and 0.24 g of tetraisopropoxytitanium to give 2.61 g (48.3%) of di[2-(3,4-dihydro-6-hydroxy-2,5,7,8-tetramethyl-2H-benzopyranyl)ethyl] malonate.

FD mass spectrum: [M]+ 568.

SYNTHESIS EXAMPLE 12

SYNTHESIS EXAMPLES 13 TO 21

The same reaction and isolation procedures as Synthesis Example 1 were followed except that 10 millimoles each of the 2-substituted ethyl alcohols of Table 2 and 5 millimoles of adipoyl chloride were used in lieu of 2.5 g of 3,4-dihydro-2-(2-hydroxyethyl)-2,5,7,8-tetramethyl-2H-benzopyran-6-ol and 5 millimoles of succinyl chloride to give the corresponding 3,4-dihydro-2H-benzopyran derivative. The results are given in Table 2.

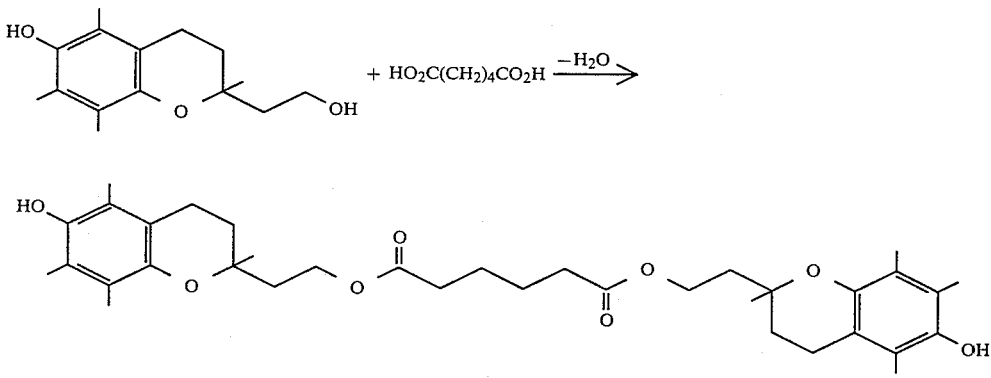

A mixture of 1.46 g of adipic acid, 5.0 g of 2,3-dihydro-2-(2-hydroxyethyl)-2,5,7,8-tetramethyl-2H-benzo-

TABLE 2

| Synthesis Example | 2-Substituted ethyl alcohol | 3,4-Dihydro-2H—benzopyran derivative Structural formula | Yield (%) | FD mass spectrum |
|---|---|---|---|---|
| 13 | | ![](bis-ester structure) | 64 | [M]+ 526 |

TABLE 2-continued
| Synthesis Example | 2-Substituted ethyl alcohol | 3,4-Dihydro-2H—benzopyran derivative Structural formula | Yield (%) | FD mass spectrum |
|---|---|---|---|---|
| 14 | 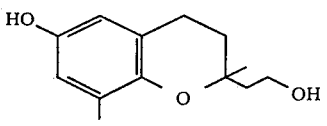 | 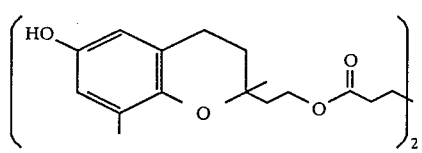 | 71 | [M]+ 554 |
| 15 | 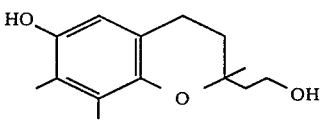 | 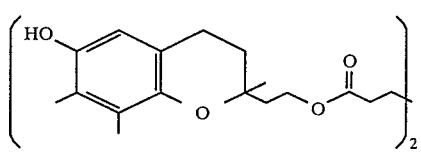 | 76 | [M]+ 582 |
| 16 | 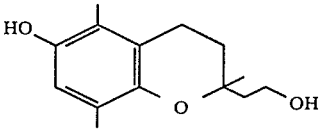 | 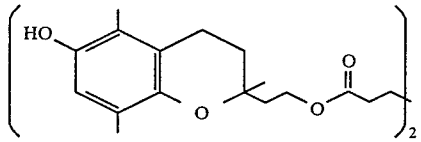 | 75 | [M]+ 582 |
| 17 | 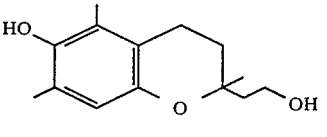 | 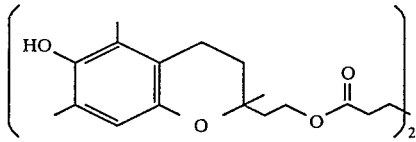 | 83 | [M]+ 582 |
| 18 | 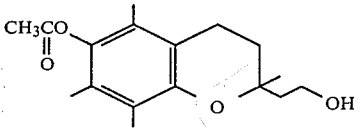 | 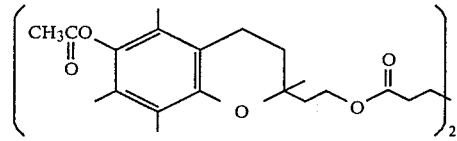 | 87 | [M]+ 694 |
| 19 | 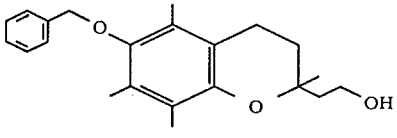 | 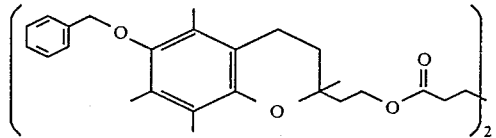 | 92 | [M]+ 790 |
| 20 | 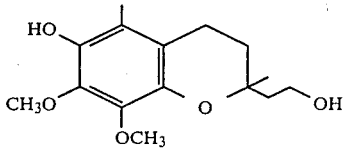 | 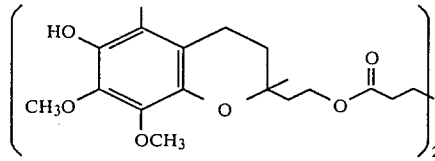 | 63 | [M]+ 674 |
| 21 | 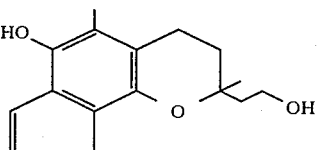 | 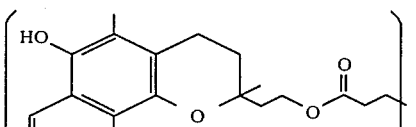 | 82 | [M]+ 654 |

SYNTHESIS EXAMPLE 22

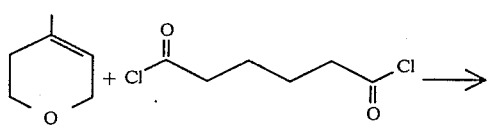

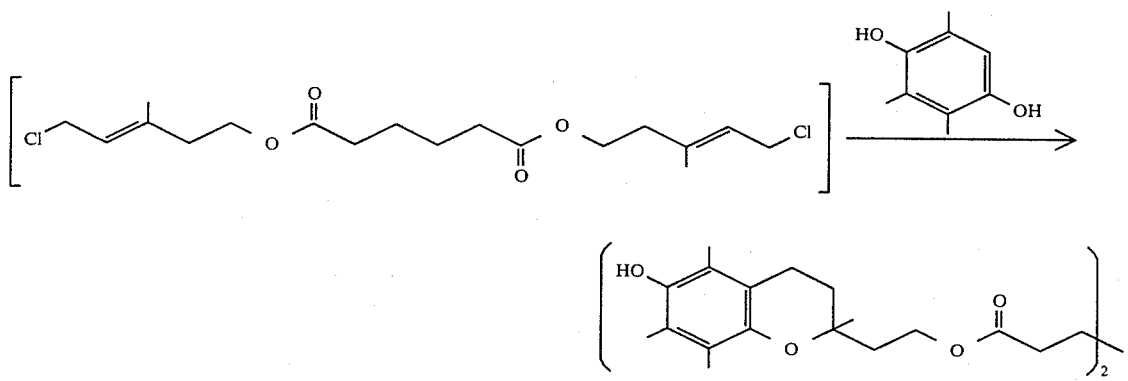

Adipoyl chloride (1.83 g) was added dropwise to a mixture of 1.96 g of 5,6-dihydro-4-methyl-2H-pyran, 10 ml of 1,2-dichloroethane and 0.08 g of anhydrous zinc chloride. The mixture was stirred at room temperature for an hour. The resulting reaction solution was then added dropwise under reflux to a mixture of 3.04 g of trimethylhydroquinone, 0.05 g of anhydrous zinc chloride and 18 ml of 1,2-dichloroethane. After completion of addition, the mixture was refluxed for 2 hours, cooled, poured into water and extracted with diethyl ether. The extract was washed with water and dried. The low-boiling substances were distilled off and the concentrate was purified by silica gel column (chromatography to give 4.25 g (69.7%) of di[2-(3,4-dihydro-6-hydroxy-2,5,7,8-tetramethyl-2H-benzopyranyl)ethyl] adipate. Identification of the product was performed in the same manner as Synthesis Example 3.

SYNTHESIS EXAMPLES 23 TO 28

The same reaction and isolation procedures as Synthesis Example 22 were followed except that 10 millimoles each of the dicarboxylic acid chlorides of Table 3 was used in lieu of 1.83 g of adipoyl chloride to give the corresponding 3,4-dihydro-2H-benzopyran derivative. The identification of these products was performed in the same manner as Synthesis Examples 2 and 4 through 8. The results are shown in Table 3.

TABLE 3

| Synthesis Example | Dicarboxylic acid chloride | Yield (%) |
|---|---|---|
| 23 | Glutaroyl chloride | 71.4 |
| 24 | Azelaoyl chloride | 74.9 |
| 25 | Sebacoyl chloride | 68.2 |
| 26 | Phthaloyl chloride | 58.7 |
| 27 | Terephthaloyl chloride | 62.6 |
| 28 | 1,10-Decanedicarbonyl bromide | 67.4 |

SYNTHESIS EXAMPLE 29 AND 30

The same reaction and isolation procedures as Synthesis Example 22 were followed except that 4.28 g of 4-benzoyloxyphenol or 3.32 g of 4-acetoxy-2-methylphenol was used in lieu of 3.04 g of trimethylhydroquinone to give the corresponding 3,4-dihydro-2H-benzopyran derivatives. The yield and FD mass spectrum of each product are given in Table 4.

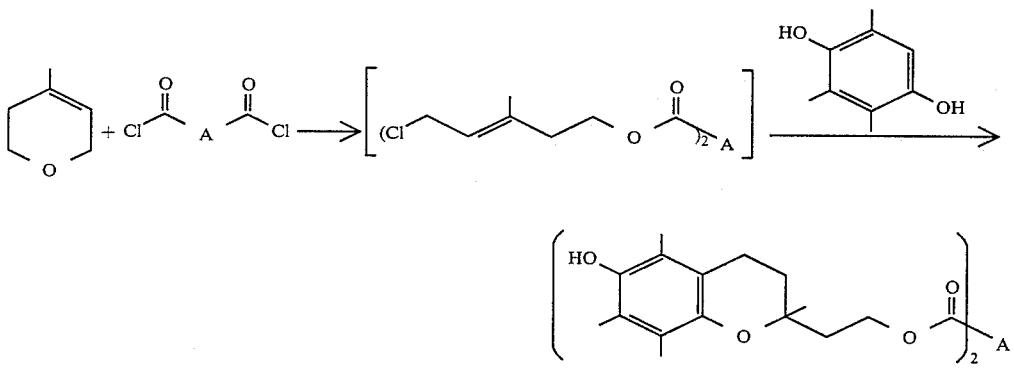

TABLE 4

| Synthesis Example | Product | Yield (%) | FD mass spectrum |
|---|---|---|---|
| 29 | 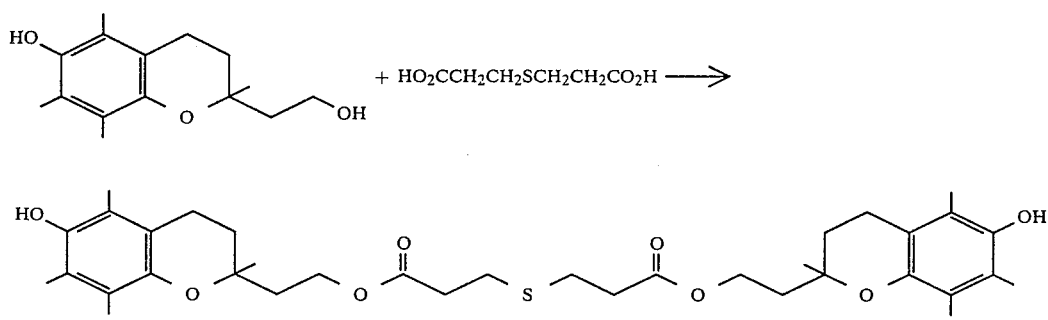 | 59.2 | [M]+ 734 |
| 30 | | 56.8 | [M]+ 638 |

SYNTHESIS EXAMPLE 31

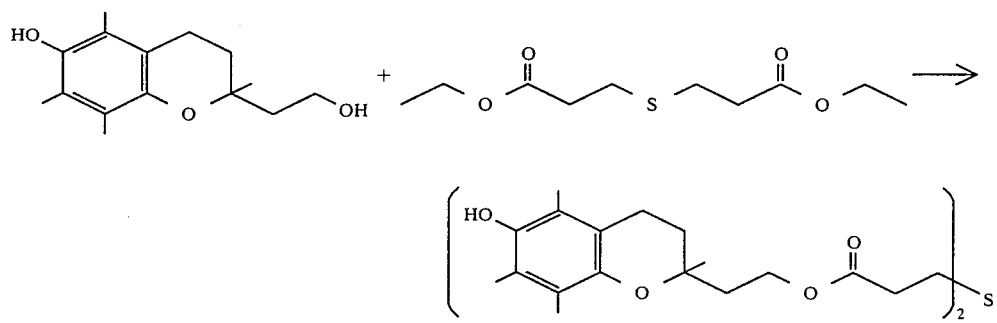

A mixture of 5.0 g of 3,4-dihydro-2-(2-hydroxyethyl)-2,5,7,8-tetramethyl-2H-benzopyran-6-ol, 1.78 g of thiodipropionic acid, 0.3 g of p-toluenesulfonic acid and 100 ml of toluene was heated in a nitrogen atmosphere and refluxed for 20 hours, with the byproduct water being azeotropically removed. The reaction mixture was then concentrated and purified by silica gel column chromatography to give 5.27 g (82%) of di[2-(3,4-dihydro-6-hydroxy-2,5,7,8-tetramethyl-2H-benzopyranyl)ethyl] 3,3'-thiodipropionate, which showed the following spectra.

NMR spectrum (90 MHz) $\delta_{CDCl_3}^{HMS}$: 1.2 (s, 6H); 1.68–2.17 (m, 26H); 2.37–2.9 (m, 12H); 3.7–4.5 (m, 6H).

FD mass spectrum: [M]+ 642.

SYNTHESIS EXAMPLE 32

The same reaction and isolation procedures as Synthesis Example 31 were followed except that 2.34 g of ethyl thiodipropionate was used in lieu of 1.78 g of thiodipropionic acid to give 5.23 g (81%) of di[2-(3,4-dihydro-6-hydroxy-2,5,7,8-tetramethyl-2H-benzopyranyl)ethyl] 3,3'-thiodipropionate.

SYNTHESIS EXAMPLE 33

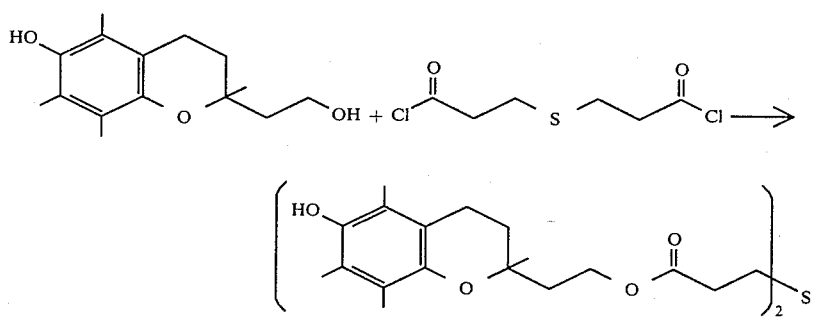

A solution of 1.6 g of pyridine and 10 ml of methylene chloride was added dropwise to a solution of 5.0 g of 3,4-dihydro-2-(2-hydroxyethyl)-2,5,7,8-tetramethyl-2H-benzopyran-6-ol and 2.2 g of thiodipropionyl chloride in 50 ml of methylene chloride in a nitrogen atmosphere. After completion of addition, the mixture was stirred at room temperature overnight, poured into water and extracted with diethyl ether. The extract was washed with diluted hydrochloric acid and saturated aqueous sodium chloride, dried over anhydrous magnesium sulfate, and concentrated. The concentrate was purified by silica gel column chromatography to give 5.64 g (88%) of di[2-(3,4-dihydro-6-hydroxy-2,5,7,8-tetramethyl-2H-benzopyranyl)ethyl]3,3'-thiodipropionate.

SYNTHESIS EXAMPLES 34 TO 41

The same reaction and isolation procedures as Synthesis Example 31 were followed except that 20 millimoles each of the 2-substituted ethyl alcohols of Table 5 was used in lieu of 5.0 g of 3,4-dihydro-2-(2-hydroxyethyl)-2,5,7,8-tetramethyl-2H-benzopyran-6-ol to give the corresponding thiodipropionic acid ester. The results are given in Table 5.

TABLE 5

| Synthesis Example | 2-Substituted ethyl alcohol | Thiodipropionic acid ester Structural formula | Yield (%) | FD mass spectrum |
|---|---|---|---|---|
| 34 | (chroman with HO-phenyl, -CH2CH2OH) | (bis-ester via thiodipropionate, S linkage, ×2) | 76 | [M]+ 558 |
| 35 | (methyl-substituted chroman-ethanol) | (corresponding thiodipropionate diester) | 79 | [M]+ 586 |
| 36 | (dimethyl-substituted chroman-ethanol) | (corresponding thiodipropionate diester) | 72 | [M]+ 614 |
| 37 | (dimethyl-substituted chroman-ethanol) | (corresponding thiodipropionate diester) | 75 | [M]+ 614 |
| 38 | (dimethyl-substituted chroman-ethanol) | (corresponding thiodipropionate diester) | 81 | [M]+ 614 |
| 39 | (benzyloxy trimethyl chroman-ethanol) | (corresponding thiodipropionate diester) | 90 | [M]+ 822 |

TABLE 5-continued

| Synthesis Example | 2-Substituted ethyl alcohol | Thiodipropionic acid ester Structural formula | Yield (%) | FD mass spectrum |
|---|---|---|---|---|
| 40 | (chroman with HO, CH₃O, OCH₃, CH₃ substituents, ethyl-OH side chain) | (bis-ester via thiodipropionate, S linking two chroman units) | 76 | [M]⁺ 706 |
| 41 | (naphthochroman with HO, CH₃ substituents, ethyl-OH side chain) | (bis-ester via thiodipropionate, S linking two naphthochroman units) | 82 | [M]⁺ 686 |

SYNTHESIS EXAMPLE 42

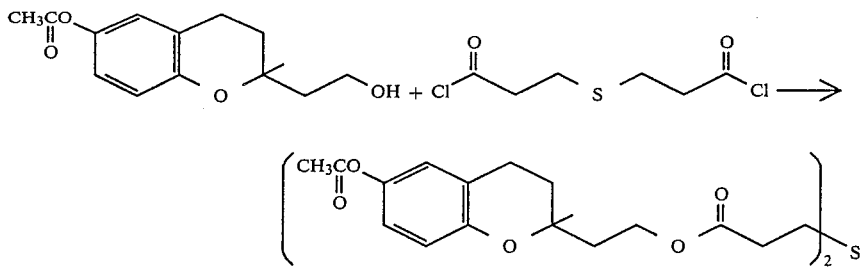

The same reaction and isolation procedures as Synthesis Example 33 were followed except that 5.0 g of 2-(6-acetoxy-3,4-dihydro-2-methyl-2H-benzopyranyl)ethanol was used in lieu of 5.0 g of 3,4-dihydro-2-(2-hydroxyethyl)-2,5,7,8-tetramethyl-2H-benzopyran-6-ol to give 5.81 g (80%) of di[2-(6-acetoxy-3,4-dihydro-2-methyl-2H-benzopyranyl)ethyl]3,3'-thiodipropionate, which showed the following FD mass spectrum.

FD mass spectrum: [M]+ 642

SYNTHESIS EXAMPLE 43

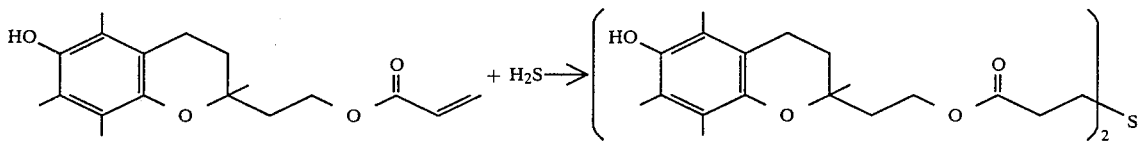

In a nitrogen atmosphere, 10 millimoles of hydrogen sulfide was bubbled into a solution consisting of 6.08 g of 2-(6-hydroxy-3,4-dihydro-2,5,7,8-tetramethyl-2H-benzopyranyl)ethyl acrylate, 0.1 g of sodium ethylate and 50 ml of tetrahydrofuran. The reaction mixture was stirred at room temperature overnight, poured into water and extracted with diethyl ether. The extract was washed with water, dried over anhydrous magnesium sulfate and concentrated. The concentrate was purified by silica gel column chromatography to give 4.72 g (73.5%) of di[2-(6-hydroxy-3,4-dihydro-2,5,7,8-tetramethyl-2H-benzopyranyl)ethyl]3,3'-thiodipropionate.

SYNTHESIS EXAMPLE 44

The same reaction and isolation procedures as Synthesis Example 43 were followed except that 0.1 ml of triethylamine was used in lieu of 0.1 g of sodium ethylate to give 4.28 g (67%) of di[2-(6-hydroxy-3,4-dihydro-2,5,7,8-tetramethyl-2H-benzopyranyl)ethyl]3,3'-thiodipropionate.

SYNTHESIS EXAMPLES 45 TO 53

The same reaction and isolation procedures as Synthesis Example 43 were followed except that 20 millimoles each of the 2-substituted ethyl acrylate was used in lieu of 6.08 g of 2-(6-hydroxy-3,4-dihydro-2,5,7,8-tetramethyl-2H-benzopyranyl)ethyl acrylate to give the corresponding thiodipropionic acid ester. Identification of these products was performed in the same manner as Synthesis Examples 34–42. The yields of the respective products are given in Table 6.

TABLE 6

| Synthesis Example | 2-Substituted ethyl acrylate | Yield (%) |
|---|---|---|
| 45 | ![structure] | 73 |
| 46 | ![structure] | 78 |
| 47 | ![structure] | 62 |

TABLE 6-continued
| Synthesis Example | 2-Substituted ethyl acrylate | Yield (%) |
|---|---|---|
| 48 | | 69 |
| 49 | | 83 |
| 50 | | 85 |
| 51 | | 64 |
| 52 | | 75 |
| 53 | | 76 |
SYNTHESIS EXAMPLE 54
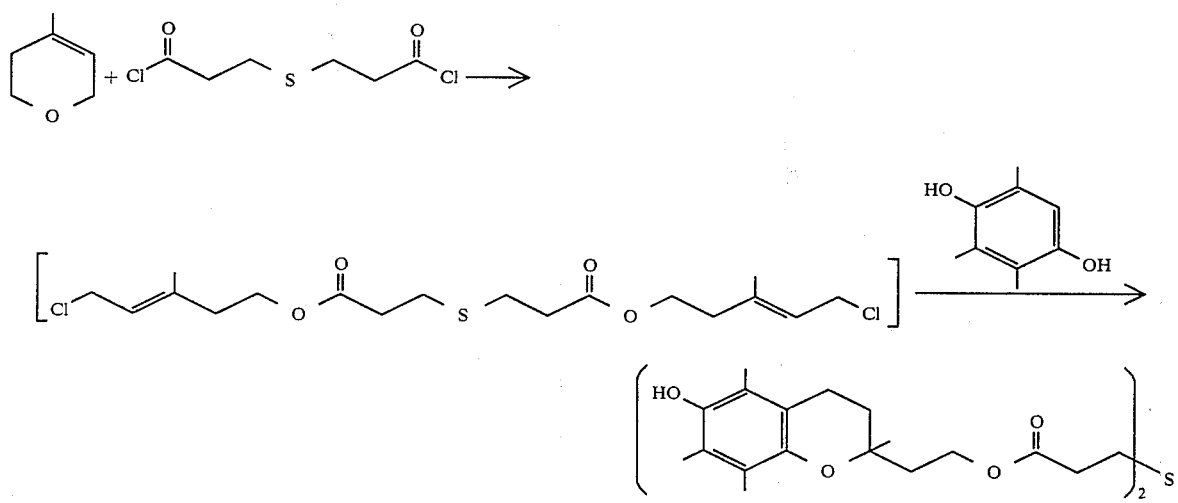
Thiodipropionyl chloride (2.15 g) was added dropwise to a mixture of 1.96 g of 5,6-dihydro-4-methyl-2H-pyran, 10 ml of 1,2-dichloroethane and 0.08 g of anhydrous zinc chloride. The mixture was stirred at room temperature for an hour, and the resulting reaction solution was added dropwise to a mixture of 3.04 g of trimethylhydroquinone, 0.05 g of anhydrous zinc chloride and 18 ml of 1,2-dichloroethane under reflux. After completion of addition, the mixture was refluxed for 2 hours, cooled, poured into water and extracted with diethyl ether. The extract was washed with water and dried. The low-boiling substances were distilled off and the concentrate was purified by silica gel column chromatography to give 4.51 g (70%) of di[2-(3,4-dihydro-6-hydroxy-2,5,7,8-tetramethyl-2H-benzopyranyl)ethyl]3,3′-thiodipropionate.

SYNTHESIS EXAMPLES 55 TO 57

The same reaction and isolation procedures as Synthesis Example 54 were followed except that 20 millimoles each of the hydroquinone derivatives mentioned in Table 7 was used in lieu of 3.04 g trimethylhydroquinone to give the corresponding thiodipropionic acid ester. Identification of these products was performed in the same manner as Synthesis Examples 38, 39 and 42. The yields of the respective products are given in Table 7.

TABLE 7

| Synthesis Example | Hydroquinone derivative | Yield (%) |
|---|---|---|
| 55 | | 64 |
| 56 | | 71 |
| 57 | 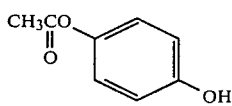 | 70 |

SYNTHESIS EXAMPLE 58

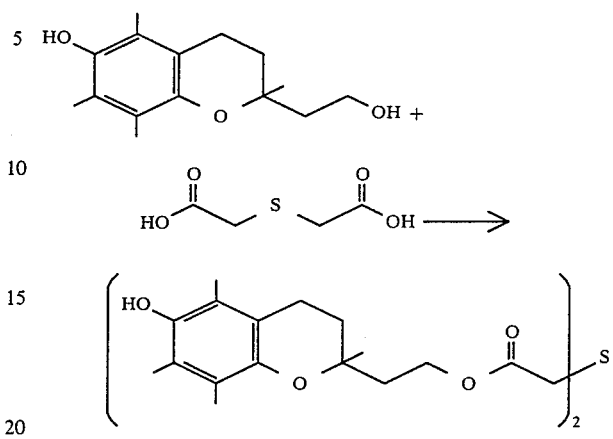

A solution of 2.5 g of 3,4-dihydro-2-(2-hydroxyethyl)-2,5,7,8-tetramethyl-2H-benzopyran-6-ol, 5 millimoles of thiodiglycolic acid and 0.1 g of p-toluenesulfonic acid in 100 ml of toluene was refluxed, while distilling off by byproduct water from the reaction system. The reaction mixture was cooled and diethyl ether was added thereto. Then, mixture was washed with water, dried over anhydrous magnesium sulfate and concentrated. The concentrate was purified by silica gel column chromatography to give 1.79 g (58%) of di[2-(3,4-dihydro-6-hydroxy-2,5,7,8-tetramethyl-2H-benzopyranyl)ethyl] thiodiacetate, which showed the following properties.

FD mass spectrum: [M]+ 614.

NMR spectrum (90 MHz) $\delta_{HMS}^{CDCl_3}$: 1.22 (s,6H); 1.55–2.2 (m, 26H); 2.56 (t, J=6 Hz, 4H); 3.3 (s, 4H); 4.05–4.53 (m, 6H).

SYNTHESIS EXAMPLES 59 TO 63

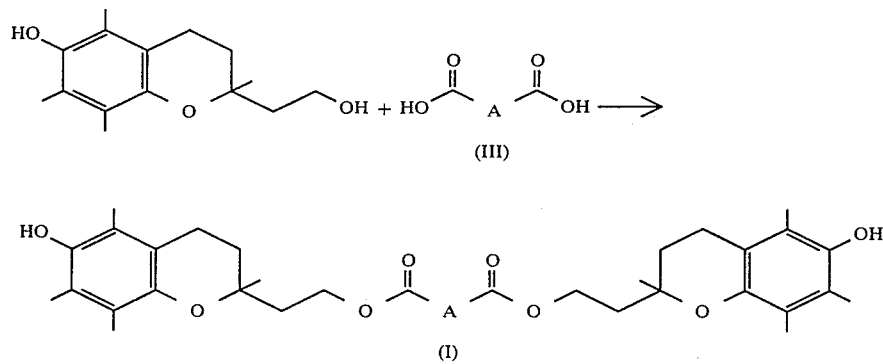

The same reaction and isolation procedures as Synthesis Example 58 were followed except that 5 millimoles each of 3-thia-1,6-hexanedioic acid, 3,4-dithia-1,6-hexanedioic acid, 4,5-dithia-1,8-octanedioic acid, 3,5-dithia-1,7-heptanedioic acid or 4,6-dithia-1,9-nonanedioic acid was used in lieu of 5 millimoles of thiodiglycolic acid to give the corresponding dicarboxylic acid diester. The yield, NMR spectrum and FD mass spectrum of each product are given in Table 8.

TABLE 8

| Synthesis Example | Dicarboxylic acid (III) | Dicarboxylic acid diester (I) | | |
|---|---|---|---|---|
| | | Yield (%) | NMR spectrum (90 MHz) $\delta_{HMS}^{CDCl_3}$ | FD mass spectrum |
| 59 | $HO_2CCH_2SCH_2CH_2CO_2H$ | 61 | 1.22(s,6H);1.6~2.2(m,26H); 2.45~3.0(m,8H);3.16(s,2H); 4.0~4.55(m,6H) | $[M]^+$ 628 |
| 60 | $HO_2CCH_2SSCH_2CO_2H$ | 37 | 1.22(s,6H);1.6~2.2(m,26H); 2.56(t,J = 6H,4H);3.3(s,4H); 4.05~4.5(m,6H) | $[M]^+$ 646 |
| 61 | $HO_2CCH_2CH_2SSCH_2CH_2CO_2H$ | 45 | 1.22(s,6H);1.6~2.2(m,26H); 2.4~3.0(m,12H);4.0~4.5(m,6H) | $[M]^+$ 674 |
| 62 | $HO_2CCH_2SCH_2SCH_2CO_2H$ | 83 | 1.23(s,6H);1.6~2.2(m,26H); 2.57(t,J = 7Hz,4H);3.27(s,4H); 3.86(s,2H);4.05~4.55(m,6H) | $[M]^+$ 660 |
| 63 | $HO_2CCH_2CH_2SCH_2SCH_2CH_2CO_2H$ | 81 | 1.23(s,6H);1.6~2.2(m,26H); 2.4~3.0(m,12H);3.86(s,2H); 4.0~4.5(m,6H) | $[M]^+$ 688 |

SYNTHESIS EXAMPLE 64

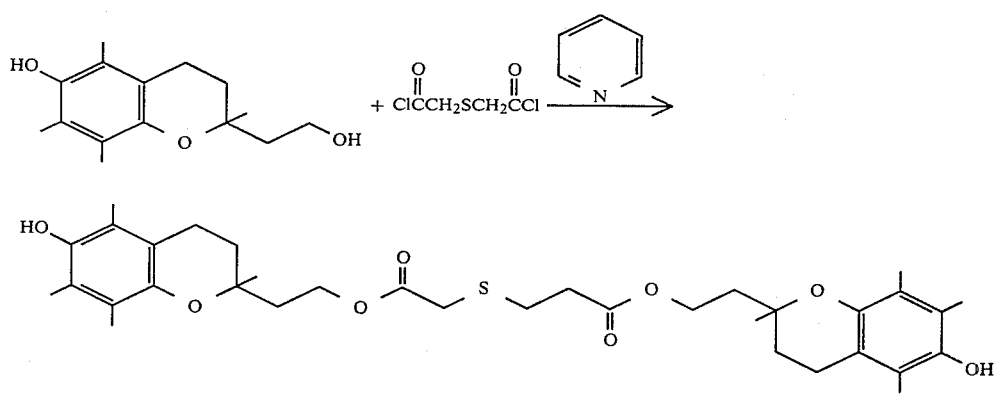

Thiodiglycoloyl dichloride (5 mmol) was added dropwise, with ice-cooling, to a mixture of 2.5 g of 3,4-dihydro-2-(2-hydroxyethyl)-2,5,7,8-tetramethyl-2H-benzopyran-6-ol, 0.79 g of pyridine and 10 ml of methylene chloride. The mixture was stirred at room temperature overnight and water was added thereto. The resulting mixture was extracted with diethyl ether, and the extract was washed with water, dried over anhydrous magnesium sulfate and concentrated. The concentrate was purified by silica gel column chromatography to give 2.82 g (92%) of di-[2-(3,4-dihydro-6-hydroxy-2,5,7,8-tetramethyl-2H-benzopyranyl)ethyl] thiodiacetate.

SYNTHESIS EXAMPLES 65 TO 72

The same reaction and isolation procedures as Synthesis Example 58 were followed except that 10 millimoles each of the 2-substituted ethyl alcohols in Table 9 was used in lieu of 2.5 g of 3,4-dihydro-2-(2-hydroxyethyl)-2,5,7,8-tetramethyl-2H-benzopyran-6-ol to give the corresponding thiodiglycolic acid diester. The results are given in Table 9.

TABLE 9

| Synthesis Example | 2-Substituted ethyl alcohol | Thiodiglycolic acid diester Structural formula | Yield (%) | FD mass spectrum |
|---|---|---|---|---|
| 65 | | | 75 | [M]⁺ 530 |
| 66 | | | 70 | [M]⁺ 558 |
| 67 | | | 71 | [M]⁺ 586 |
| 68 | | | 68 | [M]⁺ 586 |
| 69 | | | 85 | [M]⁺ 586 |
| 70 | | | 91 | [M]⁺ 794 |

TABLE 9-continued

| Synthesis Example | 2-Substituted ethyl alcohol | Thiodiglycolic acid diester | | |
|---|---|---|---|---|
| | Structural formula | Structural formula | Yield (%) | FD mass spectrum |
| 71 | [structure: chromanol with OCH3, CH3O, HO, CH3 substituents and CH2CH2OH] | [structure: (chromanyl-CH2CH2-O-C(=O)-CH2-)2S] | 72 | [M]+ 678 |
| 41 | [structure: naphthochromanol with CH3, HO substituents and CH2CH2OH] | [structure: (naphthochromanyl-CH2CH2-O-C(=O)-CH2-)2S] | 78 | [M]+ 658 |

SYNTHESIS EXAMPLE 73

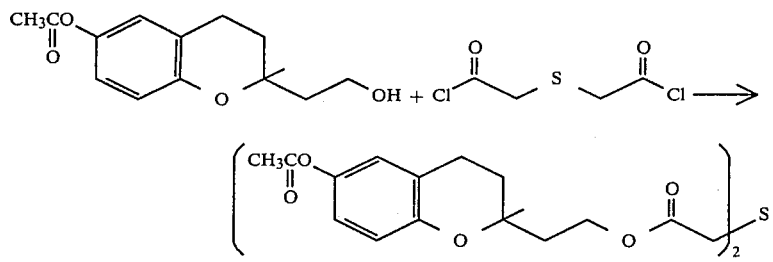

The same reaction and isolation procedures as Synthesis Example 64 were followed except that 2.5 g of 2-(6-acetoxy-3,4-dihydro-2-methyl-2H-benzopyranyl)ethanol was used in lieu of 2.5 g of 3,4-dihydro-2-(2-hydroxyethyl)-2,5,7,8-tetramethyl-2H-benzopyran-6-ol to give 2.8 g (91%) of di-[2-(6-acetoxy-3,4-dihydro-2-methyl-2H-benzopyranyl)ethyl] thiodiacetate, which showed the following FD mass spectrum.

FD mass spectrum: $[M]^+$ 614.

SYNTHESIS EXAMPLE 74

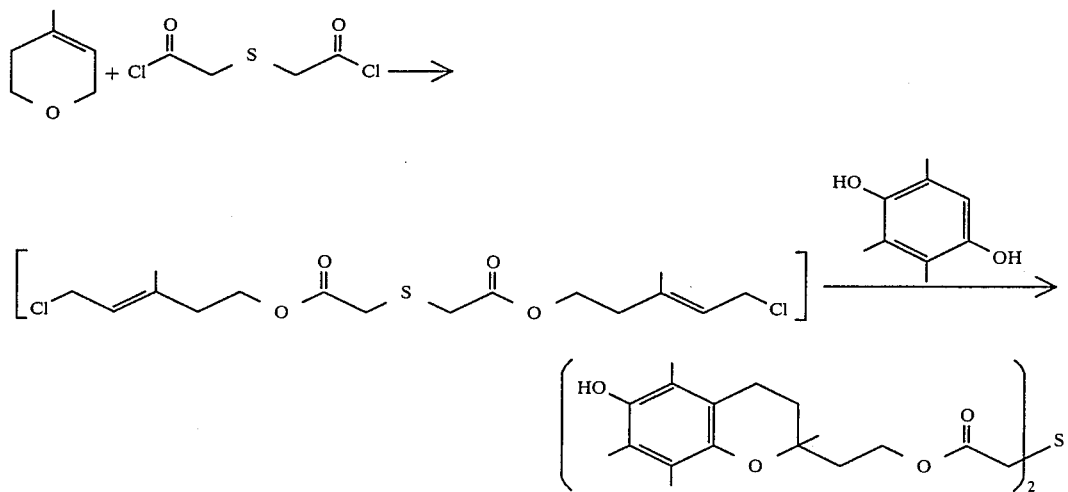

Thiodiglycoloyl dichloride (1.87 g) was added dropwise to a mixture of 1.96 g of 5,6-dihydro-4-methyl-2H-pyran, 10 ml of 1,2-dichloroethane and 0.08 g of anhydrous zinc chloride. The mixture was stirred at room temperature for an hour, and the resulting reaction solution was added dropwise to a mixture of 3.04 g of trimethylhydroquinone, 0.05 g of anhydrous zinc chloride and 18 ml of 1,2-dichloroethane under reflux. After completion of addition, the mixture was refluxed for 2 hours, cooled, poured into water and extracted with diethyl ether. The extract was washed with water and dried. The low-boiling substances were distilled off and the concentrate was purified by silica gel column chromatography to give 4.33 g (71%) of di-[2-(3,4-dihydro-6-hydroxy-2,5,7,8-tetramethyl-2H-benzopyranyl)ethyl]thiodiacetate.

SYNTHESIS EXAMPLES 75 TO 77

The same reaction and isolation procedures as Synthesis Example 74 were followed except that 20 millimoles each of the hydroquinone derivatives in Table 10 was used in lieu of 3.04 g of trimethylhydroquinone to give the corresponding thiodiglycolic acid diester. Identification of these products was performed in the same manner as Synthesis Examples 69, 70 and 73. The yields of the respective products are given in Table 10.

TABLE 10

| Synthesis Example | Hydroquinone derivative | Yield (%) |
|---|---|---|
| 75 | ![structure: 2,3-dimethylhydroquinone with HO and OH] | 68 |
| 76 | ![structure: benzyl-substituted dimethylhydroquinone] | 74 |
| 77 | ![structure: CH3CO-O-phenyl-OH (4-acetoxyphenol)] | 70 |

SYNTHESIS EXAMPLES 78 TO 81

The same reaction and isolation procedures as Synthesis Example 74 were followed except that 10 millimoles each of 3-thia-1,6-hexanedioyl dichloride, 3,4-dithia-1,6-hexanedioyl dichloride, 4,5-dithia-1,8- octanedioyl dibromide or 3,5-dithia-1,7-heptanedioyl dichloride was used in lieu of 1.87 g of thiodiglycoloyl dichloride to give the corresponding dicarboxylic acid diester. Identification of these products was performed in the same manner as Synthesis Examples 59, 60, 61 and 62. The yields of the respective products are given in Table 11.

TABLE 11

| Synthesis Example | Dicarboxylic acid dihalide | Yield (%) |
|---|---|---|
| 78 | ClCCH$_2$SCH$_2$CH$_2$CCl (with two C=O) | 72 |
| 79 | ClCCH$_2$SSCH$_2$CCl (with two C=O) | 65 |
| 80 | BrCCH$_2$CH$_2$SSCH$_2$CH$_2$CBr (with two C=O) | 63 |
| 81 | ClCCH$_2$SCH$_2$SCH$_2$CCl (with two C=O) | 74 |

SYNTHESIS EXAMPLE 82

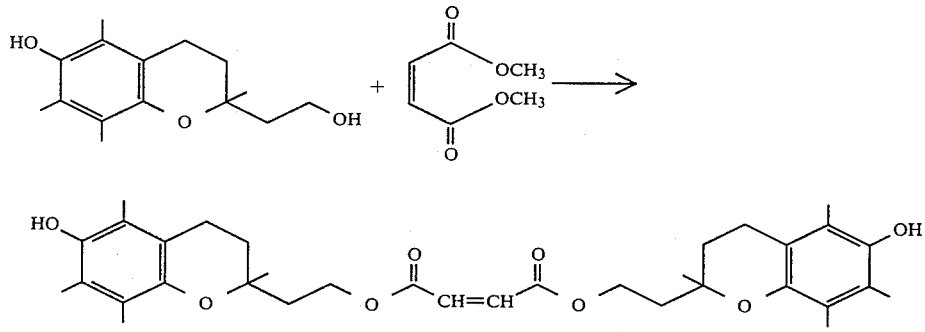

A solution of 10 g of 3,4-dihydro-2-(2-hydroxyethyl)-2,5,7,8-tetramethyl-2H-benzopyran-6-ol, 3.16 g of dimethyl maleate, 0.6 g of p-toluenesulfonic acid and 0.16 g of hydroquinone in 100 ml of toluene was heated, while distilling off the byproduct methanol gradually from the reaction system. The reaction mixture was poured into water and extracted with diethyl ether and the extract was washed with water and dried. The low-boiling substances were then distilled off under reduced pressure. The concentrate was purified by silica gel column chromatography to give 5.93 g (51%) of di[2-(3,4-dihydro-6-hydroxy-2,5,7,8-tetramethyl-2H-benzopyranyl)ethyl]maleate, which showed the following properties.

FD mass spectrum: [M]+ 580.

NMR spectrum (90 MHz) $\delta_{CDCl_3}^{HMS}$: 1.2 (s, 6H), 1.6–2.3 (m, 26H); 2.56 (t, J=7 Hz, 4H); 4.1–4.6 (m, 6H); 6.1–6.25 (m, 2H).

SYNTHESIS EXAMPLE 83

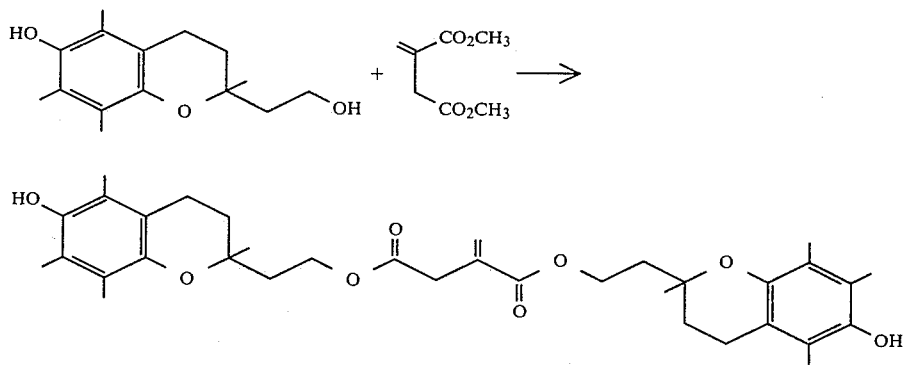

The same reaction and isolation procedures as Synthesis Example 82 were followed except that 3.16 g of dimethyl itaconate was used in lieu of 3.16 g of dimethyl maleate to give 9.04 g (76%) of di[2-(3,4-dihydro-6-hydroxy-2,5,7,8-tetramethyl-2H-benzopyranyl)ethyl]itaconate, which showed the following properties.

FD mass spectrum: [M]+ 594

NMR spectrum (90 MHz) $\delta_{CDCl_3}^{HMS}$: 1.22 (s, 6H); 1.6–2.2 (m, 26H); 2.57 (t, J=7 Hz, 4H); 3.3 (s, 2H); 4.1–4.5 (m, 6H); 5.67 (s, 1H); 6.3 (s, 1H).

SYNTHESIS EXAMPLE 84

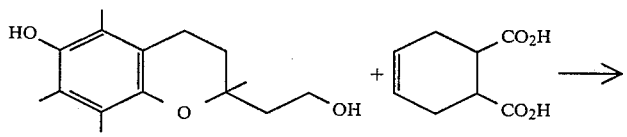

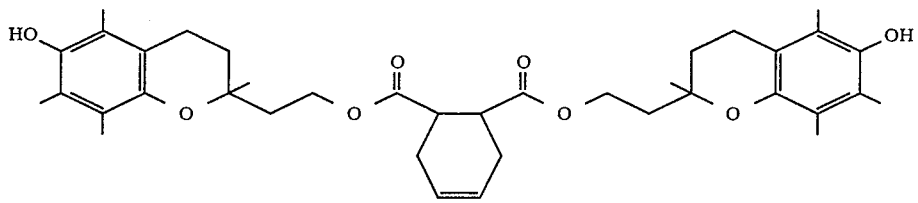

A solution of 5.0 g of 3,4-dihydro-2-(2-hydroxyethyl)-2,5,7,8-tetramethyl-2H-benzopyran-6-ol, 1.70 g of 4-cyclohexene-1,2-dicarboxylic acid, 0.16 g of p-toluenesulfonic acid and 0.04 g of hydroquinone in 100 ml of toluene was heated, while distilling off the byproduct water from the reaction system. After cooling, water was added to the reaction mixture and the resulting mixture was extracted with diethyl ether. The extract was washed with water and dried over anhydrous magnesium sulfate. The low-boiling substances were then distilled off under reduced pressure. The concentrate was purified by silica gel column chromatography to give 5.12 g (81%) of di[2-(3,4-dihydro-6-hydroxy-2,5,7,8-tetramethyl-2H-benzopyranyl)ethyl]4-cyclohexene-1,2-dicarboxylate, which had the following properties.

FD mass spectrum: [M]+ 634.

NMR spectrum (90 MHz) $\delta_{CDCl_3}^{HMS}$: 1.2 (s, 6H); 1.6–3.1 (m, 36H); 4.06–4.4 (m, 6H); 5.62 (s, 2H).

SYNTHESIS EXAMPLE 85

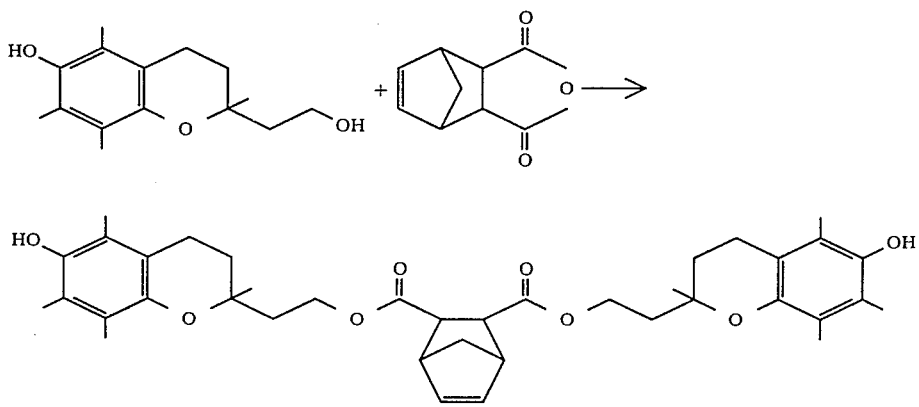

A solution of 5.0 g of 3,4-dihydro-2-(2-hydroxyethyl)-2,5,7,8-tetramethyl-2H-benzopyran-6-ol, 1.64 g of 5-norbornene-2,3-dicarboxylic anhydride, 0.1 g of p-toluenesulfonic acid and 0.1 g of hydroquinone in 100 ml of toluene was heated, while distilling off the byproduct water from the reaction system. After cooling, water was added and the mixture was extracted with diethyl ether. The extract was washed with water and dried over anhydrous magnesium sulfate. The low-boiling substances were then distilled off under reduced pressure. The concentrate was purified by silica gel column chromatography to give 5.1 g (79%) of di[2-(3,4-dihydro-6-hydroxy-2,5,7,8-tetramethyl-2H-benzopyranyl)ethyl]5-norbornene-2,3-dicarboxylate, which had the following properties.

FD mass spectrum: [M]+ 646.

NMR spectrum (90 MHz) $\delta_{CDCl_3}^{HMS}$: 1.2 (s, 6H); 1.4–3.3 (m, 36H); 4.0–4.5 (m, 4H): 4.6–4.83 (m, 2H); 4.87 (s, 2H).

SYNTHESIS EXAMPLES 86 TO 92

The same reaction and isolation procedures as Synthesis Example 85 were followed except that 1.52 g of 1-cyclohexene-1,2-dicarboxylic anhydride, 1.54 g of cyclohexane-1,2-dicarboxylic anhydride, 1.12 g of citraconic anhydride, 1.66 g of norbornane-2,3-dicarboxylic anhydride, 3.71 g of 1,4,5,6,7,7-hexachloro-5-norbornene-2,3-dicarboxylic anhydride, 1.66 g of 4-methyl-4-cyclohexene-1,2-dicarboxylic anhydride or 1.78 g of 5-methyl-5-norbornene-2,3-dicarboxylic anhydride was used in lieu of 1.64 g of 5-norbornene-2,3-dicarboxylic anhydride to give the corresponding 3,4-dihydro-2H-benzopyran derivative. The results are given in Table 12.

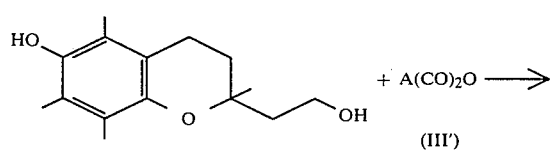

-continued
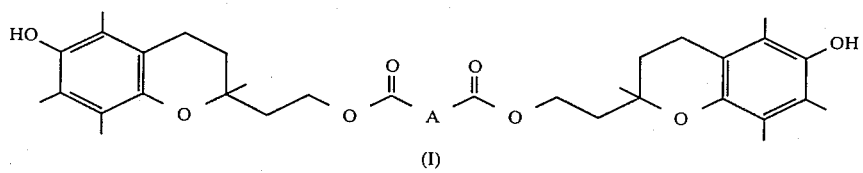
(I)
TABLE 12
| Synthesis Example | Carboxylic anhydride (III') | 3,4-Dihydro-2H—benzopyran derivative (I) | | |
|---|---|---|---|---|
| | | A | Yield (%) | FD mass spectrum |
| 86 | | | 83 | [M]+ 634 |
| 87 | | | 88 | [M]+ 636 |
| 88 | | —C=CH—<br>     |<br>   CH$_3$ | | 76 | [M]+ 594 |
| 89 | | | 89 | [M]+ 648 |
| 90 | | | 77 | [M]+ 850<br>[M + 2]+ 852<br>[M + 4]+ 854 |
| 91 | | | 85 | [M]+ 648 |

TABLE 12-continued

| Synthesis Example | Carboxylic anhydride (III') | 3,4-Dihydro-2H—benzopyran derivative (I) | | |
|---|---|---|---|---|
| | | A | Yield (%) | FD mass spectrum |
| 92 | 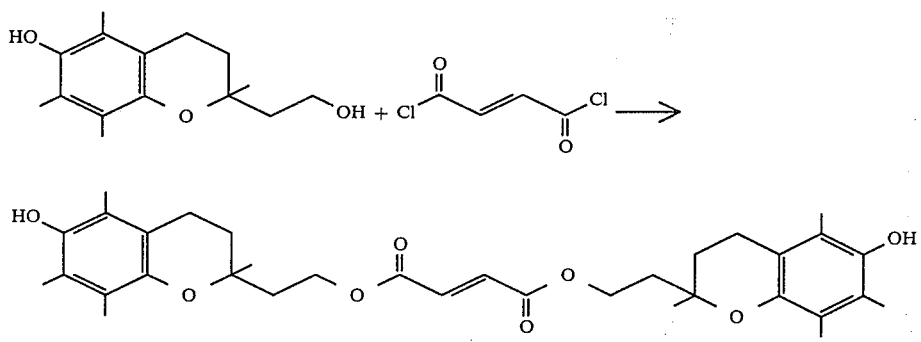 | | 84 | [M]+ 660 |

SYNTHESIS EXAMPLE 93

Fumaroyl dichloride (1.53 g) was added dropwise to a solution of 5.0 g of 3,4-dihydro-2-(2-hydroxyethyl)-2,5,7,8-tetramethyl-2H-benzopyran-6-ol and 1.6 g of pyridine in 40 ml of methylene chloride. The mixture was stirred at room temperature for 4 hours. The resulting reaction solution was poured into water and extracted with diethyl ether. The extract was washed with water and dried. The low-boiling substances were then distilled off under reduced pressure. The concentrate was purified by silica gel column chromatography to give 5.14 g (89%) of di[2-(3,4-dihydro-6-hydroxy-2,5,7,8-tetramethyl-2H-benzopyranyl)ethyl]fumarate, which showed the following spectrum.

FD mass spectrum: [M]+ 580.

SYNTHESIS EXAMPLES 94 TO 101

The same reaction and isolation procedures as Synthesis Example 82 were followed except that 40 millimoles each of the 2-substituted ethyl alcohol in Table 13 was used in lieu of 10 g of 3,4-dihydro-2-(2-hydroxyethyl)-2,5,7,8-tetramethyl-2H-benzopyran-6-ol to give the corresponding 3,4-dihydro-2H-benzopyran derivative. The results are given in Table 13.

TABLE 13

| Synthesis Example | 2-Substituted ethyl alcohol | Yield (%) | FD mass spectrum |
|---|---|---|---|
| 94 | | 67 | [M]+ 496 |
| 95 | | 72 | [M]+ 524 |
| 96 | | 80 | [M]+ 552 |
| 97 | | 81 | [M]+ 552 |

TABLE 13-continued

| Synthesis Example | 2-Substituted ethyl alcohol | Yield (%) | FD mass spectrum |
|---|---|---|---|
| 98 | | 86 | [M]+ 552 |
| 99 | | 92 | [M]+ 760 |
| 100 | | 85 | [M]+ 644 |
| 101 | | 82 | [M]+ 624 |

SYNTHESIS EXAMPLE 102

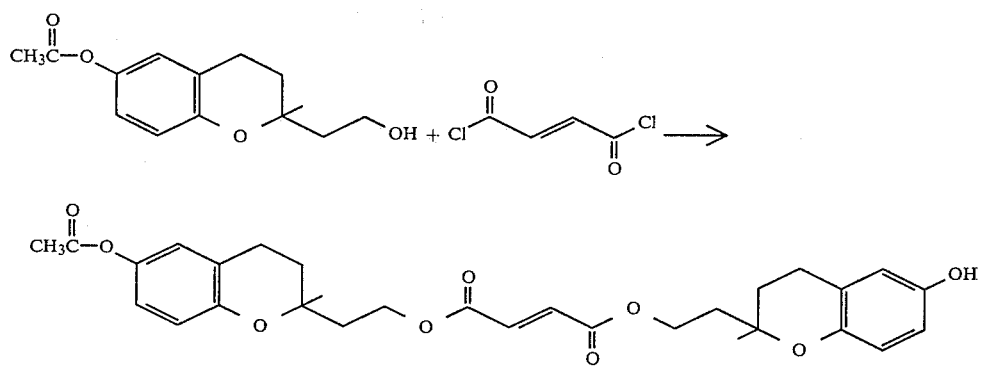

The same reaction and isolation procedures as Synthesis Example 93 were followed except that 5.0 g of 2-(6-acetoxy-3,4-dihydro-2-methyl-2H-benzopyranyl)ethanol was used in lieu of 5.0 g of 3,4-dihydro-2-(2-hydroxyethyl)-2,5,7,8-tetramethyl-2H-benzopyran-6-ol to give 5.26 g (91%) of di[2-(6-acetoxy-3,4-dihydro-2-methyl-2H-benzopyranyl)ethyl]fumarate, which showed the following FD mass spectrum.

FD mass spectrum: [M]+ 580.

TEST EXAMPLES 1 THROUGH 19

To each 100 g of ethyl linoleate was added 0.020 g of one of the test compounds indicated in Table 14 to prepare a test solution. A 20 ml portion of each test solution was exposed to the accelerated conditions of aeration of 2.33 cc/sec. at 97.8° C. in an AOM (Antioxygen Method) tester and the time period till the POV (peroxide value) reached 100 meq/kg was determined. The results are presented in Table 14.

TABLE 14

| Test Example | Test compound | Time (hrs.) till POV = 100 meq/kg |
|---|---|---|
| 1 | No addition | 0.2 |
| 2 | BHT[(1)] | 3.0 |
| 3 | α-Tocopherol | 3.2 |

TABLE 14-continued

| Test Example | Test compound | Time (hrs.) till POV = 100 meq/kg |
|---|---|---|
| 4 | (structure) | 4.8 |
| 5 | (structure) | 4.3 |
| 6 | (structure) | 4.5 |
| 7 | (structure) | 5.6 |
| 8 | (structure) | 4.1 |
| 9 | (structure) | 5.0 |
| 10 | (structure) | 4.7 |
| 11 | (structure) | 4.3 |
| 12 | (structure) | 4.2 |

TABLE 14-continued

| Test Example | Test compound | Time (hrs.) till POV = 100 meq/kg |
|---|---|---|
| 13 | 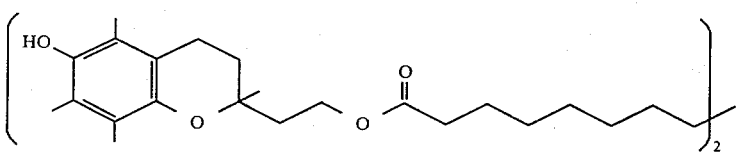 | 4.2 |
| 14 | 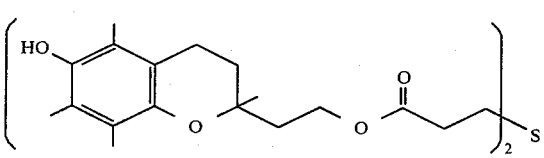 | 5.8 |
| 15 | 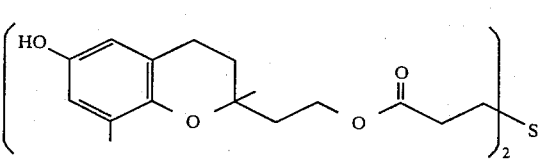 | 5.1 |
| 16 | 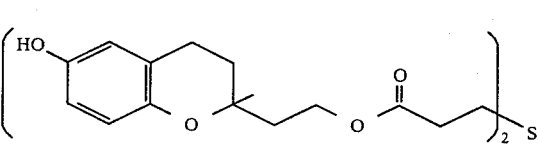 | 5.0 |
| 17 | 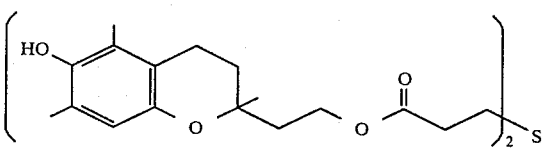 | 5.5 |
| 18 | 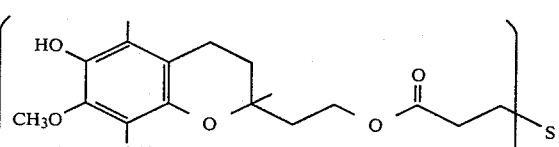 | 5.9 |
| 19 | 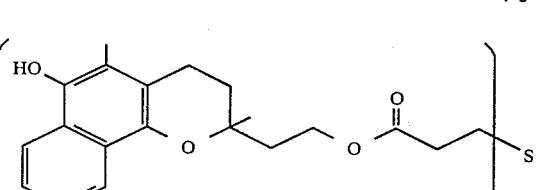 | 5.2 |

Note
[1] 3,5-Di-tert-butyl-4-hydroxytoluene

TEST EXAMPLES 20 THROUGH 32

To each 100 g of ethyl linoleate was added 0.020 g of one of the test compounds indicated in Table 15 to prepare a test solution. A 20 ml portion of the solution was exposed to the accelerated conditions of aeration of 2.33 cc/sec. at 97.8° C. in an AOM (Antioxygen Method) tester and the time period till the POV (peroxide value) reached 100 meq/kg was determined. The results are presented in Table 15.

TABLE 15

| Test Example | Test Compound | Time (hrs.) till POV = 100 meq/kg |
|---|---|---|
| 20 | No addition | 0.2 |
| 21 | BHT | 1.0 |
| 22 | Irganox 1010[2] | 0.8 |

TABLE 15-continued
| Test Example | Test Compound | Time (hrs.) till POV = 100 meq/kg |
|---|---|---|
| 23 | α-Tocopherol | 1.2 |
| 24 | 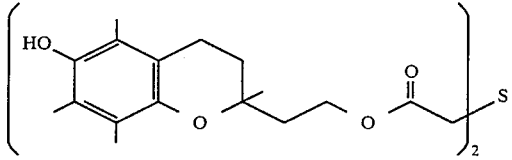 | 2.5 |
| 25 | 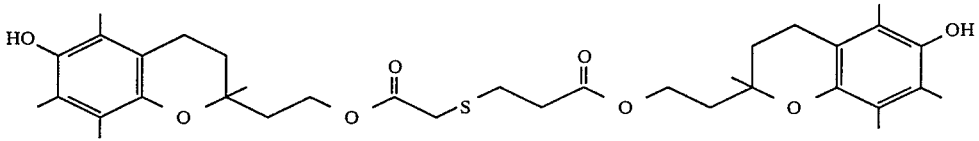 | 2.0 |
| 26 | 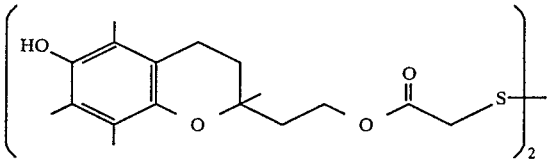 | 2.2 |
| 27 | 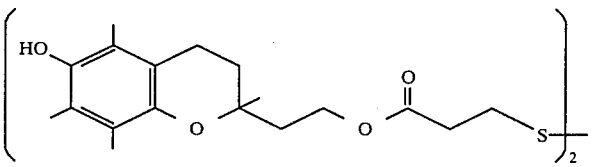 | 2.1 |
| 28 | 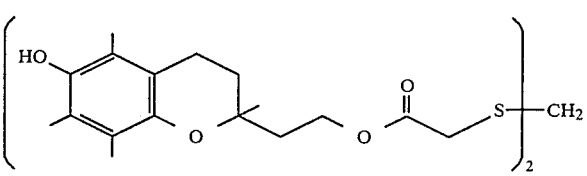 | 2.4 |
| 29 | 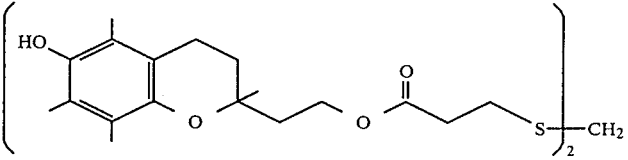 | 2.3 |
| 30 | 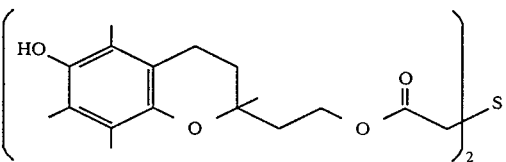 | 2.4 |
| 31 | 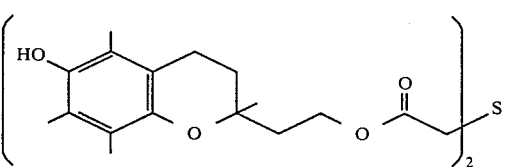 | 2.4 |

TABLE 15-continued

| Test Example | Test Compound | Time (hrs.) till POV = 100 meq/kg |
|---|---|---|
| 32 | [structure] | 2.5 |

(2) Commercial product: Pentaerythrytol tetrakis [3-(3,5-di-tert-butyl-4-hydroxyphenyl) propionate]

TEST EXAMPLES 33 THROUGH 51

To each 100 g of ethyl linoleate was added 0.020 g of one of the test compounds indicated in Table 16 to prepare a test solution. A 20 ml of the test solution was exposed to the accelerated conditions of aeration of 2.33 cc/sec. at 97.8° C. in an AOM (Antioxygen Method) tester and the time period till the POV (peroxide value) reached 100 meq/kg was determined. The results are presented in Table 16.

TABLE 16

| Test Example | Test compound | Time (hrs.) till POV = 100 meq/kg |
|---|---|---|
| 33 | No addition | 0.1 |
| 34 | BHT | 0.7 |
| 35 | α-Tocopherol | 0.8 |
| 36 | [structure] | 2.0 |
| 37 | [structure] | 2.0 |
| 38 | [structure] | 2.3 |
| 39 | [structure] | 2.8 |
| 40 | [structure] | 2.4 |

TABLE 16-continued

| Test Example | Test compound | Time (hrs.) till POV = 100 meq/kg |
|---|---|---|
| 41 | [chemical structure: bis-chromanol maleate diester] | 1.8 |
| 42 | [chemical structure: bis-chromanol cyclohexane-1,2-dicarboxylate diester] | 1.9 |
| 43 | [chemical structure: bis-chromanol norbornane-2,3-dicarboxylate diester] | 1.8 |
| 44 | [chemical structure: bis-chromanol hexachloronorbornene-dicarboxylate diester] | 1.6 |
| 45 | [chemical structure: bis-chromanol 4-methylcyclohex-4-ene-1,2-dicarboxylate diester] | 1.8 |
| 46 | [chemical structure: bis-chromanol methylnorbornene-dicarboxylate diester] | 1.8 |
| 47 | [chemical structure: bis-chromanol fumarate diester] | 1.9 |

TABLE 16-continued

| Test Example | Test compound | Time (hrs.) till POV = 100 meq/kg |
|---|---|---|
| 48 | (structure: bis-chromanol maleate, with methyl substituents) | 1.7 |
| 49 | (structure: bis-chromanol maleate, with dimethyl substituents) | 1.9 |
| 50 | (structure: bis-chromanol maleate, with methyl and dimethoxy substituents) | 2.1 |
| 51 | (structure: bis-naphthochromanol maleate) | 1.6 |

WORKING EFFECT EXAMPLES 1 THROUGH 9

Anti-aging test with polyisoprene rubber

A high-cis-1,4-polyisoprene rubber (Kuraprene IR-10, viscosity-average molecular weight 850,000; manufactured by Kuraray Isoprene Chemical Co., Ltd.) containing 0.3 PHR of each test compound was subjected to an aging test in an oven at 100° C. for predetermined time periods and the plasticity (Pt) of the aged polyisoprene rubber and the plasticity (Po) of unaged polyisoprene rubber were determined with a Wallace rapid plastimeter. The plasticity retention index (PRI) (%)=(Pt/Po)×100 was calculated. The results are presented in Table 17.

TABLE 17

| Working Effect Example | Test Compound | PRI (%) (Aging Time) | | |
|---|---|---|---|---|
| | | 4 hrs. | 8 hrs. | 16 hrs. |
| Control | Irganox 1010 | 42 | 22 | 8 |
| Control | α-Tocopherol | 46 | 26 | 15 |
| 1 | (chromanol propionate dimer structure) | 77 | 47 | 33 |
| 2 | (chromanol butyrate dimer structure) | 77 | 65 | 35 |

TABLE 17-continued

| Working Effect Example | Test Compound | PRI (%) (Aging Time) | | |
|---|---|---|---|---|
| | | 4 hrs. | 8 hrs. | 16 hrs. |
| 3 | [structure] | 90 | 70 | 39 |
| 4 | [structure] | 97 | 79 | 48 |
| 5 | [structure] | 95 | 67 | 49 |
| 6 | [structure] | 99 | 75 | 55 |
| 7 | [structure] | 80 | 63 | 27 |
| 8 | [structure] | 70 | 48 | 36 |
| 9 | [structure] | 81 | 65 | 45 |

WORKING EFFECT EXAMPLES 10 THROUGH 18

Aging test of polypropylene

A polypropylene (NOVATEC-P 4500J, melt index: 8.0, density: 0.90; manufactured by Mitsubishi Kasei Kogyo Kabushiki Kaisha) containing 0.1 PHR of one of the test compounds was milled in a plastograph at 240° C. and 30 r.p.m. to investigate the time course of mixing torque (m.g). The results are presented in Table 18.

TABLE 18
| Working Effect Example | Test compound | Mixing torque (m.g) (Mixing time) | | |
|---|---|---|---|---|
| | | 3 min. | 10 min. | 20 min. |
| Control | No addition | 405 | 140 | 40 |
| Control | Irganox 1010 | 400 | 185 | 70 |
| Control | α-Tocopherol | 410 | 260 | 124 |
| 10 | 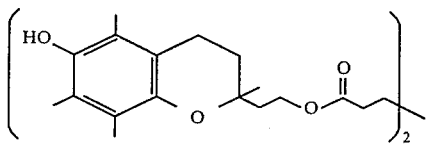 | 415 | 295 | 155 |
| 11 | 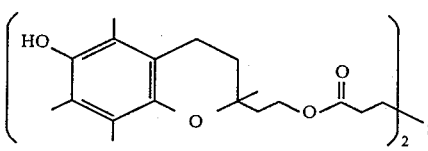 | 410 | 315 | 200 |
| 12 | 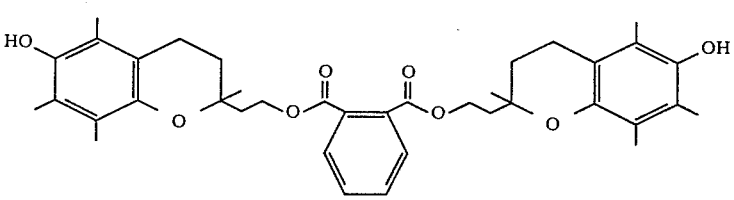 | 410 | 300 | 155 |
| 13 | 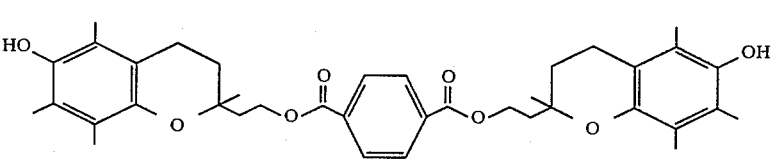 | 415 | 295 | 150 |
| 14 | 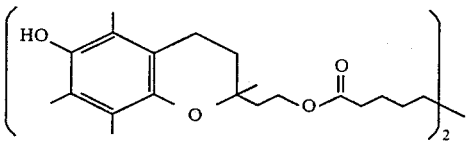 | 410 | 290 | 150 |
| 15 | 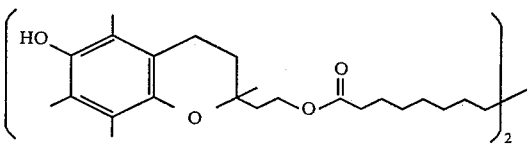 | 405 | 285 | 145 |
| 16 | 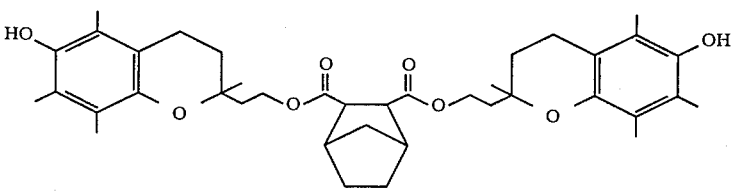 | 410 | 290 | 160 |
| 17 | 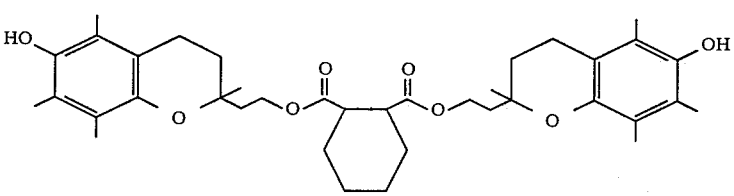 | 410 | 295 | 155 |

TABLE 18-continued

| Working Effect Example | Test compound | Mixing torque (m.g) (Mixing time) | | |
|---|---|---|---|---|
| | | 3 min. | 10 min. | 20 min. |
| 18 | 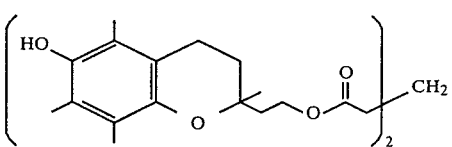 | 405 | 285 | 145 |

WORKING EFFECT EXAMPLES 19 THROUGH 22

Aging test of polyethylene

A polyethylene (LDPE F-22CE, melt index: 1.0, density: 0.924; manufactured by Nippon Petrochemicals Co., Ltd.) containing 1 PHR of one of the test compounds was milled in a plastograph at 320° C. and 30 r.p.m. to investigate the time course of mixing torque (m.g). The results are presented in Table 19.

WORKING EFFECT EXAMPLES 23 THROUGH 25

Aging test of polyurethane

A polyurethane [prepared by polymerizing polytetramethyleneglycol (molecular weight: 2,000), 4,4'-methylenebis(phenylisocyanate) and 1,4-butanediol at a ratio of 1:5:4] containing 1 PHR of each test compound was subjected to an aging test in an oven at 120° C. for 750 hours and the tensile strength of the aged polyurethane was determined. The results are presented in Table 20. The tensile strength of unaged polyurethane was 750 kg/cm².

TABLE 19

| Working Effect Example | Test Compound | Mixing torque (m.g) (Mixing time) | | |
|---|---|---|---|---|
| | | 3 min. | 10 min. | 20 min. |
| Control | No addition | 325 | 170 | 100 |
| Control | BHT | 300 | 210 | 165 |
| Control | α-Tocopherol | 290 | 205 | 140 |
| 19 | 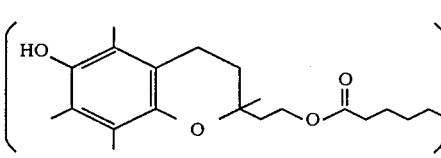 | 300 | 275 | 225 |
| 20 | 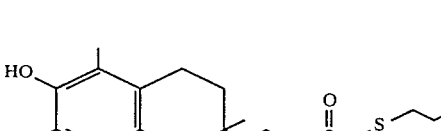 | 305 | 270 | 200 |
| 21 | | 295 | 270 | 205 |
| 22 | 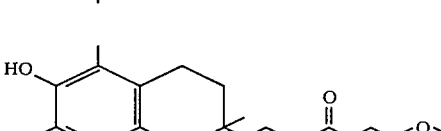 | 310 | 265 | 200 |

TABLE 20

| Working Effect Example | Test compound | Tensile strength after aging (kg/cm²) |
|---|---|---|
| Control | No addition | <50 (after 200 hours) |
| Control | Topanol CA[3] | 150 |
| Control | Irganox 565[4] | <50 |
| 23 | 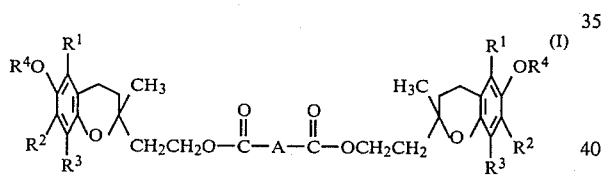 | 285 |
| 24 | 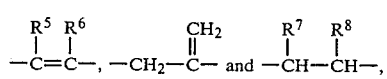 | 280 |
| 25 | 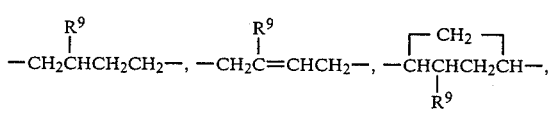 | 290 |

Note
[3] Commercial product: 1,1,3-Tris(2-methyl-4-hydroxy-5-tert-butylphenyl)butane
[4] Commercial product: 6-(4-Hydroxy-3,5-di-tert-butylanilino)-2,4-bis(octylthio)-1,3,5-triazine

What is claimed is:
1. A compound of the general formula (I)

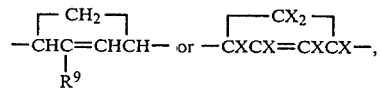

wherein $R^1$ is a hydrogen atom or a lower alkyl group; $R^2$ and $R^3$ are the same or different and each is a hydrogen atom, a lower alkyl group or a lower alkoxy group, or $R^2$ and $R^3$ taken together represent a group of the formula —CH=CH—CH=CH—; $R^4$ is a hydrogen atom or a hydroxy-protecting group; A is a group selected from the class consisting of —CH$_2$)$_n$, phenylene, —CH$_2$SCH$_2$—, —CH$_2$CH$_2$SCH$_2$—, —CH$_2$CH$_2$SCH$_2$CH$_2$—, —CH$_2$S—SCH$_2$—, —CH$_2$CH$_2$S—SCH$_2$CH$_2$—, —CH$_2$SCH$_2$SCH$_2$—, —CH$_2$CH$_2$SCH$_2$SCH$_2$CH$_2$—,

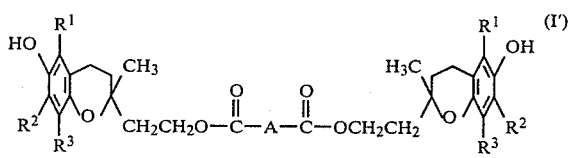

where n is an integer equal to 1 to 14; $R^5$ and $R^6$ are the same or different and each is a hydrogen atom or a lower alkyl group, or $R^5$ and $R^6$ taken together represent a group of —(CH$_2$)$_4$—; $R^7$ and $R^8$ taken together represent

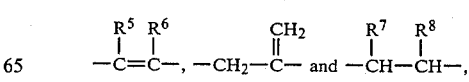

-continued $$-CHC=CHCH-  \text{ or }  -CXCX=CXCX-,$$

where $R^9$ is a hydrogen atom or a lower alkyl group and X is a halogen atom.

2. A compound according to claim 1, which has the general formula (I')

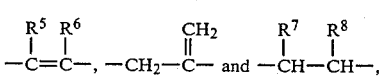

wherein $R^1$ is a hydrogen atom or a lower alkyl group; $R^2$ and $R^3$ are the same or different and each is a hydrogen atom, a lower alkyl group or a lower alkoxy group, or $R^2$ and $R^3$ taken together represent a group of the formula —CH=CH—CH=CH—; A is a group selected from the class consisting of —CH$_2$)$_n$, phenylene, —CH$_2$SCH$_2$—, —CH$_2$CH$_2$SCH$_2$—, —CH$_2$CH$_2$SCH$_2$CH$_2$—, —CH$_2$S—SCH$_2$—, —CH$_2$CH$_2$S—SCH$_2$CH$_2$—, —CH$_2$SCH$_2$SCH$_2$—, —CH$_2$CH$_2$SCH$_2$SCH$_2$CH$_2$—, where n is an integer equal to or greater than 1; $R^5$ and $R^6$ are the same or different and each is a hydrogen atom or a lower alkyl group, or $R^5$ and $R^6$ taken together represent a group of $-(CH_2)_4-$; $R^7$ and $R^8$ taken together represent

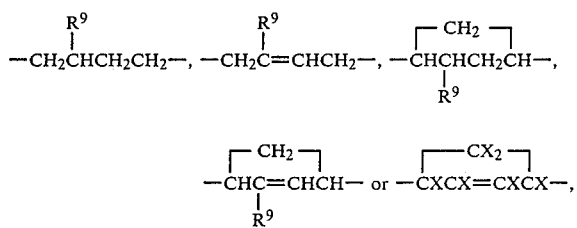

where $R^9$ is a hydrogen atom or a lower alkyl group and X is a halogen atom.

3. A compound of general formula (I') according to claim 2 wherein each of $R^1$, $R^2$ and $R^3$ is a methyl group.

4. A compound according to claim 3 which is di[2-(3,4-dihydro-6-hydroxy-2,5,7,8-tetramethyl-2H-benzopyranyl)ethyl]succinate.

5. A compound according to claim 3 which is di[2-(3,4-dihydro-6-hydroxy-2,5,7,8-tetramethyl-2H-benzopyranyl)ethyl]adipate.

6. A compound according to claim 3 which is di[2-(3,4-dihydro-6-hydroxy-2,5,7,8-tetramethyl-2H-benzopyranyl)ethyl]glutarate.

7. A compound according to claim 3 which is di[2-(3,4-dihydro-6-hydroxy-2,5,7,8-tetramethyl-2H-benzopyranyl)ethyl]sebacate.

8. A compound according to claim 3 which is di[2-(3,4-dihydro-6-hydroxy-2,5,7,8-tetramethyl-2H-benzopyranyl)ethyl]hexadecanedioate.

9. A compound according to claim 3 which is di[2-(3,4-dihydro-6-hydroxy-2,5,7,8-tetramethyl-2H-benzopyranyl)ethyl]phthalate.

10. A compound according to claim 3 which is di[2-(3,4-dihydro-6-hydroxy-2,5,7,8-tetramethyl-2H-benzopyranyl)ethyl]terephthalate.

11. A compound according to claim 3 which is di[2-(3,4-dihydro-6-hydroxy-2,5,7,8-tetramethyl-2H-benzopyranyl)ethyl]3,3'-thiodipropionate.

12. A compound according to claim 3 which is di[2-(3,4-dihydro-6-hydroxy-2,5,7,8-tetramethyl-2H-benzopyranyl)ethyl]thiodiacetate.

13. A compound according to claim 3 which is di[2-(3,4-dihydro-6-hydroxy-2,5,7,8-tetramethyl-2H-benzopyranyl)ethyl]3,5-dithia-1,7-heptanedioate.

14. A compound according to claim 3 which is di[2-(3,4-dihydro-6-hydroxy-2,5,7,8-tetramethyl-2H-benzopyranyl)ethyl]4,6-dithia-1,9-nonanedioate.

15. A compound according to claim 3 which is di[2-(3,4-dihydro-6-hydroxy-2,5,7,8-tetramethyl-2H-benzopyranyl)ethyl]3-thia-1,6-hexanedioate.

16. A compound according to claim 3 which is di[2-(3,4-dihydro-6-hydroxy-2,5,7,8-tetramethyl-2H-benzopyranyl)ethyl]maleate.

17. A compound according to claim 3 which is di[2-(3,4-dihydro-6-hydroxy-2,5,7,8-tetramethyl-2H-benzopyranyl)ethyl]fumarate.

18. A compound according to claim 3 which is di[2-(3,4-dihydro-6-hydroxy-2,5,7,8-tetramethyl-2H-benzopyranyl)ethyl]itaconate.

19. A compound according to claim 3 which is di[2-(3,4-dihydro-6-hydroxy-2,5,7,8-tetramethyl-2H-benzopyranyl)ethyl]cyclohexane-1,2-dicarboxylate.

20. A compound according to claim 3 which is di[2-(3,4-dihydro-6-hydroxy-2,5,7,8-tetramethyl-2H-benzopyranyl)ethyl]4-cyclohexene-1,2-dicarboxylate.

21. A compound according to claim 3 which is di[2-(3,4-dihydro-6-hydroxy-2,5,7,8-tetramethyl-2H-benzopyranyl)ethyl]norbornane-2,3-dicarboxylate.

22. A compound according to claim 3 which is di[2-(3,4-dihydro-6-hydroxy-2,5,7,8-tetramethyl-2H-benzopyranyl)ethyl]1,4,5,6,7,7-hexachloro-5-norbornene-2,3-dicarboxylate.

* * * * *

UNITED STATES PATENT AND TRADEMARK OFFICE
CERTIFICATE OF CORRECTION

PATENT NO. : 4,523,024
DATED : June 11, 1985
INVENTOR(S) : Manzo SHIONO, et al

It is certified that error appears in the above-identified patent and that said Letters Patent is hereby corrected as shown below:

-- At Column 1, line 30; Column 69, line 49 and Column 70, line 57 delete "$-CH_2)_n$" and insert therefor -- $(CH_2)_n$ --.

-- At Column 3, line 14, delete "$(CH_2-_n$" and insert therefor -- $(CH_2)_n$ --.

-- At Columns 11-12, TABLE 1, Synthesis Example 4, delete "$ClCO(CH_{23})_7COCl$" and insert therefor -- $ClCO(CH_2)_7COCl$ --.

-- At Columns 11-12, TABLE 1, Synthesis Example 9, delete "$(CH_2)_{10}$" and insert therefor -- $(CH_2)_{14}$ --.

-- At Column 17, lines 40-41, delete "(" --.

-- At Column 33, delete

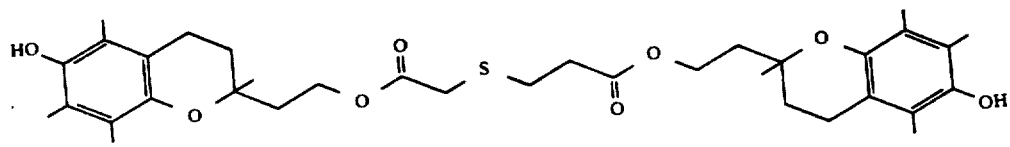

UNITED STATES PATENT AND TRADEMARK OFFICE
CERTIFICATE OF CORRECTION

PATENT NO. : 4,523,024
DATED : June 11, 1985
INVENTOR(S) : Manzo SHIONO, et al

It is certified that error appears in the above-identified patent and that said Letters Patent is hereby corrected as shown below:

and insert therefor

-- 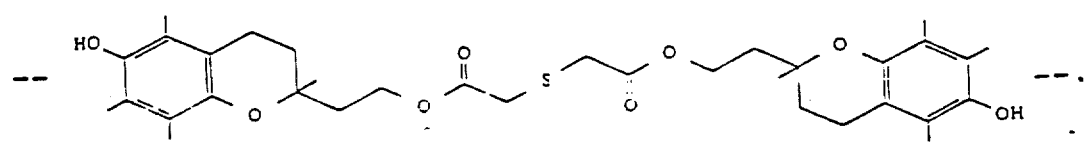 --.

-- At Columns 49-50, change

" 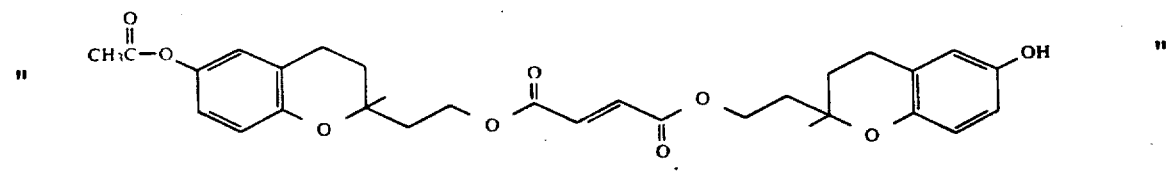 "

to

-- 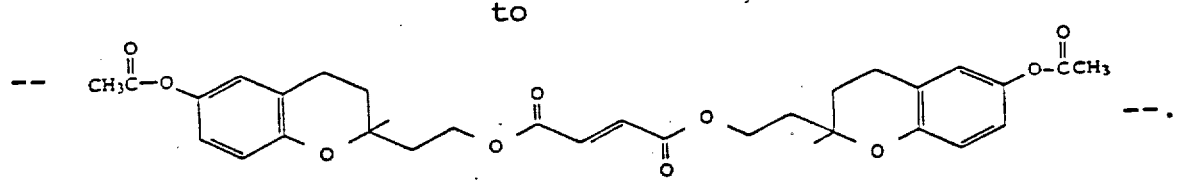 --.

UNITED STATES PATENT AND TRADEMARK OFFICE
CERTIFICATE OF CORRECTION

PATENT NO. : 4,523,024

DATED : June 11, 1985

INVENTOR(S) : Manzo SHIONO, et al

It is certified that error appears in the above-identified patent and that said Letters Patent is hereby corrected as shown below:

-- At Columns 55-56, TABLE 15, Example 30, change

"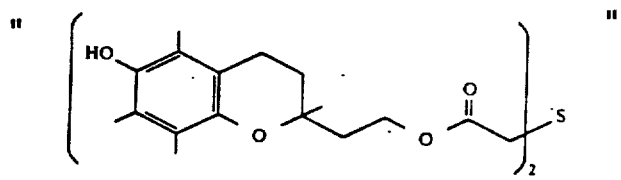"

to

-- 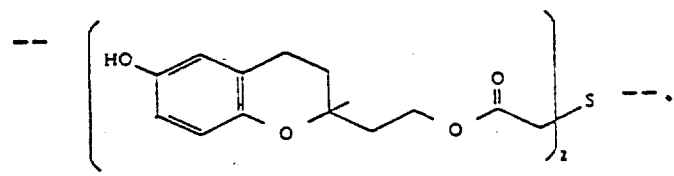 --.

-- At Columns 55-56, TABLE 15, Example 31, change

"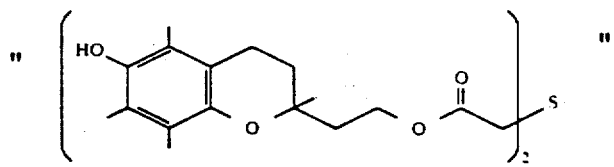"

UNITED STATES PATENT AND TRADEMARK OFFICE
CERTIFICATE OF CORRECTION

PATENT NO. : 4,523,024
DATED : June 11, 1985
INVENTOR(S) : Manzo SHIONO, et al

Page 4 of 7

It is certified that error appears in the above-identified patent and that said Letters Patent is hereby corrected as shown below:

to

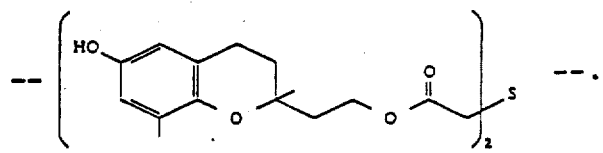

-- At Columns 57-58, TABLE 15, Example 32, change

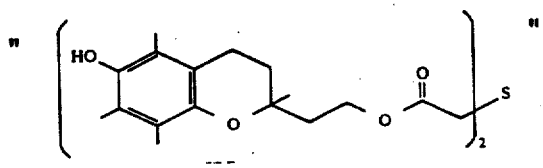

to

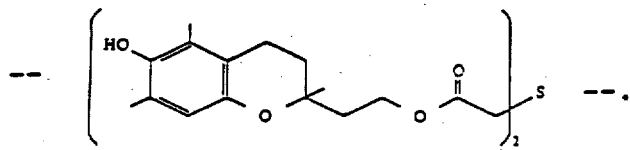

UNITED STATES PATENT AND TRADEMARK OFFICE
CERTIFICATE OF CORRECTION

PATENT NO. : 4,523,024

DATED : June 11, 1985

INVENTOR(S) : Manzo SHIONO, et al

It is certified that error appears in the above-identified patent and that said Letters Patent is hereby corrected as shown below:

-- At Columns 63-64, TABLE 17, Example 6, delete

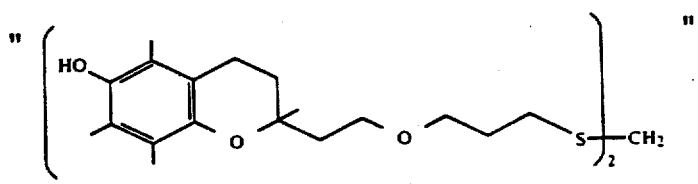

and insert therefor

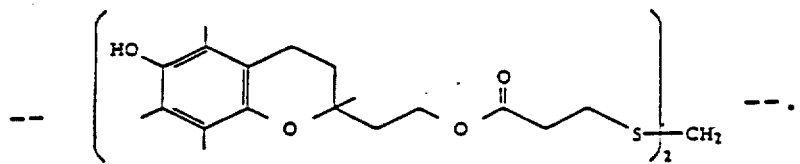

--.

-- At Columns 63-64, TABLE 17, Example 7, delete

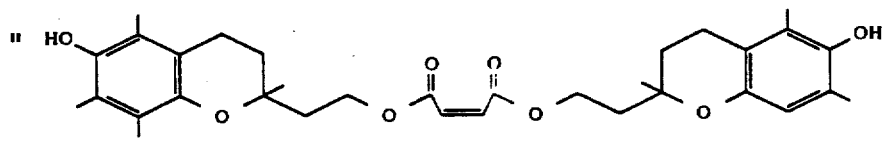

UNITED STATES PATENT AND TRADEMARK OFFICE
CERTIFICATE OF CORRECTION

PATENT NO. : 4,523,024
DATED : June 11, 1985
INVENTOR(S) : Manzo SHIONO, et al

It is certified that error appears in the above-identified patent and that said Letters Patent is hereby corrected as shown below:

and insert therefor

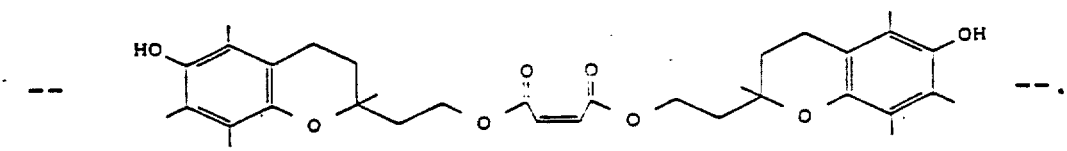

-- At Columns 63-64, TABLE 17, Example 8, delete

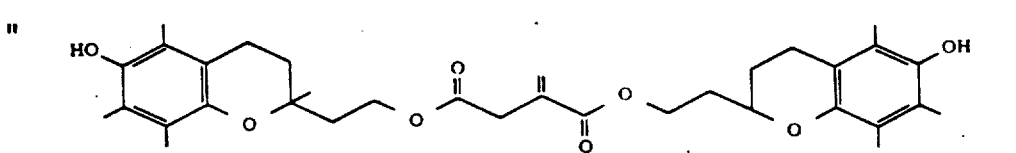

and insert therefor

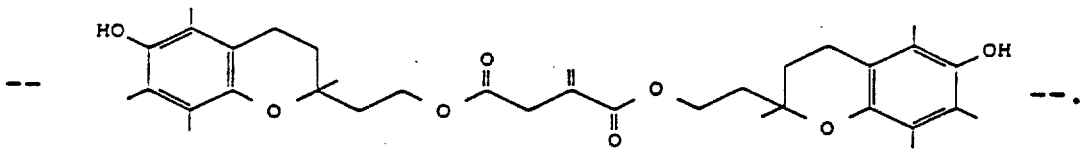

UNITED STATES PATENT AND TRADEMARK OFFICE
CERTIFICATE OF CORRECTION

PATENT NO. : 4,523,024

DATED : June 11, 1985

INVENTOR(S) : Manzo SHIONO, et al

It is certified that error appears in the above-identified patent and that said Letters Patent is hereby corrected as shown below:

-- At Columns 67-68, TABLE 19, Example 22, delete

"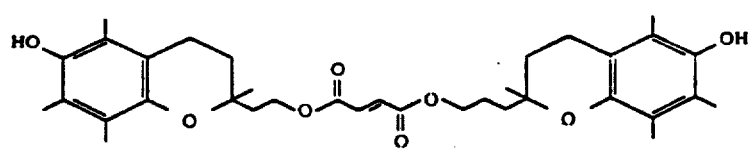"

and insert therefor

--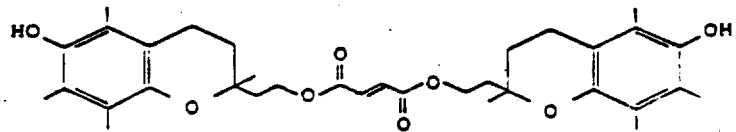--.

Signed and Sealed this

Twenty-fourth Day of February, 1987

Attest:

DONALD J. QUIGG

Attesting Officer

Commissioner of Patents and Trademarks